United States Patent
Addison et al.

(10) Patent No.: US 11,445,930 B2
(45) Date of Patent: *Sep. 20, 2022

(54) SYSTEM AND METHOD FOR DETERMINING STROKE VOLUME OF A PATIENT

(71) Applicant: Covidien LP, Mansfield, MA (US)

(72) Inventors: Paul Stanley Addison, Edinburgh (GB); James Nicholas Watson, Edinburgh (GB)

(73) Assignee: COVIDIEN LP, Mansfield, MA (US)

(*) Notice: Subject to any disclaimer, the term of this patent is extended or adjusted under 35 U.S.C. 154(b) by 93 days.

This patent is subject to a terminal disclaimer.

(21) Appl. No.: 16/588,486

(22) Filed: Sep. 30, 2019

(65) Prior Publication Data

US 2020/0022590 A1 Jan. 23, 2020

Related U.S. Application Data

(60) Continuation of application No. 14/977,301, filed on Dec. 21, 2015, now Pat. No. 10,448,851, which is a (Continued)

(51) Int. Cl.
    *A61B 5/029* (2006.01)
    *A61B 5/024* (2006.01)
    (Continued)

(52) U.S. Cl.
    CPC ............ *A61B 5/029* (2013.01); *A61B 5/024* (2013.01); *A61B 5/0261* (2013.01);
    (Continued)

(58) Field of Classification Search
    CPC .................. A61B 5/029; A61B 5/024
    See application file for complete search history.

(56) References Cited

U.S. PATENT DOCUMENTS

| 4,094,308 A | 6/1978 | Cormier |
| 4,282,655 A | 8/1981 | Tinman et al. |

(Continued)

FOREIGN PATENT DOCUMENTS

| EP | 0537383 A1 | 4/1993 |
| EP | 0841034 A1 | 5/1998 |

(Continued)

OTHER PUBLICATIONS

Alty et al., "Predicting Arterial Stiffness From the Digital Volume Pulse Waveform," IEEE Transactions on Biomedical Engineering, vol. 54, No. 12, Nov. 19, 2007, pp. 2268-2275.

(Continued)

*Primary Examiner* — Rex R Holmes
*Assistant Examiner* — Jennifer L Ghand
(74) *Attorney, Agent, or Firm* — Shumaker & Sieffert, P.A.

(57) ABSTRACT

A PPG system for determining a stroke volume of a patient includes a PPG sensor configured to be secured to an anatomical portion of the patient. The PPG sensor is configured to sense a physiological characteristic of the patient. The PPG system may include a monitor operatively connected to the PPG sensor. The monitor receives a PPG signal from the PPG sensor. The monitor includes a pulse trending module determining a slope transit time of an upslope of a primary peak of the PPG signal. The pulse trending module determines a stroke volume of the patient as a function of the slope transit time.

20 Claims, 6 Drawing Sheets

Related U.S. Application Data division of application No. 13/609,566, filed on Sep. 11, 2012, now Pat. No. 9,241,646.

(51) Int. Cl.
 *A61B 5/026* (2006.01)
 *A61B 5/00* (2006.01)
 *A61B 8/02* (2006.01)
 *A61B 5/1455* (2006.01)

(52) U.S. Cl.
 CPC .......... *A61B 5/02427* (2013.01); *A61B 5/742* (2013.01); *A61B 5/02416* (2013.01); *A61B 5/14551* (2013.01); *A61B 8/02* (2013.01)

(56) References Cited

U.S. PATENT DOCUMENTS

| | | | |
|---|---|---|---|
| 4,289,141 A | 9/1981 | Cormier | |
| 4,450,527 A | 5/1984 | Sramek | |
| 5,092,339 A | 3/1992 | Geddes et al. | |
| 5,178,151 A | 1/1993 | Sackner | |
| 5,275,159 A | 1/1994 | Griebel | |
| 5,331,960 A | 7/1994 | Krenzke | |
| 5,408,327 A | 4/1995 | Geiler et al. | |
| 5,595,182 A | 1/1997 | Krivitski | |
| 5,743,268 A | 4/1998 | Kabal | |
| 5,817,010 A | 10/1998 | Hibi | |
| 5,833,618 A | 11/1998 | Caro et al. | |
| 5,913,826 A | 6/1999 | Blank | |
| 5,935,066 A | 8/1999 | Harris | |
| 6,004,272 A | 12/1999 | Barry et al. | |
| 6,045,509 A | 4/2000 | Caro et al. | |
| 6,155,984 A | 12/2000 | Krivitski | |
| 6,292,686 B1 | 9/2001 | Chaiken et al. | |
| 6,371,921 B1 | 4/2002 | Caro et al. | |
| 6,389,306 B1 | 5/2002 | Chaiken et al. | |
| 6,503,206 B1 | 1/2003 | Li et al. | |
| 6,561,986 B2 | 5/2003 | Baura et al. | |
| 6,616,613 B1 | 9/2003 | Goodman | |
| 6,719,705 B2 | 4/2004 | Mills | |
| 6,740,072 B2 | 5/2004 | Starkweather et al. | |
| 6,754,523 B2 | 6/2004 | Toole | |
| 6,758,822 B2 | 7/2004 | Romano | |
| 6,760,608 B2 | 7/2004 | Lynn | |
| 6,776,764 B2 | 8/2004 | Pinsky | |
| 6,816,266 B2 | 11/2004 | Varshneya et al. | |
| 6,819,950 B2 | 11/2004 | Mills | |
| 6,869,402 B2 | 3/2005 | Arnold | |
| 6,875,176 B2 | 4/2005 | Mourad et al. | |
| 7,022,077 B2 | 4/2006 | Mourad et al. | |
| 7,033,320 B2 | 4/2006 | Von Behren et al. | |
| 7,035,679 B2 | 4/2006 | Addison et al. | |
| 7,056,292 B2 | 6/2006 | Hutchinson | |
| 7,171,271 B2 | 1/2007 | Koh et al. | |
| 7,220,230 B2 | 5/2007 | Roteliuk et al. | |
| 7,344,497 B2 | 3/2008 | Kline | |
| 7,367,949 B2 | 5/2008 | Korhonen et al. | |
| 7,367,954 B2 | 5/2008 | Starr et al. | |
| 7,407,486 B2 | 8/2008 | Huiku et al. | |
| 7,452,333 B2 | 11/2008 | Roteliuk | |
| 7,462,152 B2 | 12/2008 | Kolluri et al. | |
| 7,615,011 B2 | 11/2009 | Sugo et al. | |
| 7,674,231 B2 | 3/2010 | McCombie et al. | |
| 7,704,209 B2 | 4/2010 | Bennett et al. | |
| 7,747,301 B2 | 6/2010 | Cheng et al. | |
| 7,785,263 B2 | 8/2010 | Roteliuk et al. | |
| 7,806,830 B2 | 10/2010 | Bernstein | |
| 7,850,617 B2 | 12/2010 | Goedje et al. | |
| 7,881,762 B2 | 2/2011 | Kling et al. | |
| 7,887,502 B2 | 2/2011 | Ross et al. | |
| 7,894,869 B2 | 2/2011 | Hoarau | |
| 7,899,510 B2 | 3/2011 | Hoarau | |
| 7,976,472 B2 | 7/2011 | Kiani | |
| 8,073,516 B2 | 12/2011 | Scharf et al. | |
| 8,073,518 B2 | 12/2011 | Chin | |
| 8,092,386 B1 | 1/2012 | Wenzel et al. | |
| 8,187,197 B2 | 5/2012 | Shapira et al. | |
| 8,211,031 B2 | 7/2012 | Poupko et al. | |
| 8,216,136 B2 | 7/2012 | Addison et al. | |
| 8,551,006 B2 | 10/2013 | Karst et al. | |
| 8,740,806 B2 | 6/2014 | Parfenova et al. | |
| 8,768,438 B2 | 7/2014 | Mestha et al. | |
| 8,814,800 B2 | 8/2014 | Fortin et al. | |
| 8,977,348 B2 | 3/2015 | Su et al. | |
| 9,060,745 B2 | 6/2015 | Su et al. | |
| 9,241,646 B2* | 1/2016 | Addison ............. A61B 5/02427 |
| 10,448,851 B2* | 10/2019 | Addison ............... A61B 5/029 |
| 2002/0022785 A1 | 2/2002 | Romano | |
| 2002/0038078 A1 | 3/2002 | Ito | |
| 2002/0082485 A1 | 6/2002 | Faithfull et al. | |
| 2003/0167012 A1 | 9/2003 | Friedman et al. | |
| 2005/0010116 A1 | 1/2005 | Korhonen et al. | |
| 2005/0070774 A1 | 3/2005 | Addison et al. | |
| 2005/0080345 A1 | 4/2005 | Finburgh et al. | |
| 2005/0085707 A1 | 4/2005 | Korsten et al. | |
| 2005/0124903 A1 | 6/2005 | Roteliuk et al. | |
| 2005/0143665 A1 | 6/2005 | Huiku et al. | |
| 2005/0177046 A1 | 8/2005 | Mills | |
| 2005/0192488 A1 | 9/2005 | Bryenton et al. | |
| 2005/0240087 A1 | 10/2005 | Keenan et al. | |
| 2006/0167363 A1 | 7/2006 | Osypka et al. | |
| 2006/0184051 A1 | 8/2006 | Hempstead et al. | |
| 2006/0224053 A1 | 10/2006 | Black et al. | |
| 2006/0253007 A1 | 11/2006 | Cheng et al. | |
| 2006/0258921 A1 | 11/2006 | Addison et al. | |
| 2007/0093702 A1 | 4/2007 | Yu et al. | |
| 2007/0213619 A1 | 9/2007 | Linder | |
| 2007/0213625 A1 | 9/2007 | Nayak et al. | |
| 2007/0249949 A1 | 10/2007 | Hadley | |
| 2008/0082004 A1 | 4/2008 | Banet et al. | |
| 2008/0119329 A1 | 5/2008 | Punkka et al. | |
| 2008/0139958 A1 | 6/2008 | Uemura et al. | |
| 2008/0167540 A1 | 7/2008 | Korhonen et al. | |
| 2008/0183232 A1* | 7/2008 | Voss ................. A61B 5/02255 607/24 |
| 2008/0255433 A1 | 10/2008 | Prough et al. | |
| 2008/0287815 A1 | 11/2008 | Chon et al. | |
| 2009/0099459 A1 | 4/2009 | Svanberg et al. | |
| 2009/0105556 A1 | 4/2009 | Fricke et al. | |
| 2009/0149762 A1 | 6/2009 | Ou Yang et al. | |
| 2009/0163821 A1 | 6/2009 | Sola et al. | |
| 2009/0177110 A1 | 7/2009 | Lyden et al. | |
| 2009/0198140 A1 | 8/2009 | Riobo et al. | |
| 2009/0204012 A1 | 8/2009 | Joeken | |
| 2009/0240119 A1 | 9/2009 | Schwaibold et al. | |
| 2009/0326353 A1* | 12/2009 | Watson ................ A61B 5/6814 600/330 |
| 2009/0326388 A1 | 12/2009 | Watson et al. | |
| 2009/0326395 A1 | 12/2009 | Watson | |
| 2010/0016739 A1 | 1/2010 | Shelley et al. | |
| 2010/0049007 A1 | 2/2010 | Sterling et al. | |
| 2010/0049071 A1 | 2/2010 | Goor et al. | |
| 2010/0069761 A1 | 3/2010 | Karst et al. | |
| 2010/0081895 A1 | 4/2010 | Zand | |
| 2010/0152547 A1 | 6/2010 | Sterling et al. | |
| 2010/0152591 A1 | 6/2010 | Yu et al. | |
| 2010/0160794 A1 | 6/2010 | Banet et al. | |
| 2010/0191128 A1 | 7/2010 | Shelley et al. | |
| 2010/0210924 A1 | 8/2010 | Parthasarathy et al. | |
| 2010/0228102 A1 | 9/2010 | Addison et al. | |
| 2010/0249542 A1 | 9/2010 | Thijs et al. | |
| 2010/0249559 A1 | 9/2010 | Lovejoy | |
| 2010/0249612 A1 | 9/2010 | Cohen et al. | |
| 2010/0268090 A1 | 10/2010 | Rubinstein et al. | |
| 2010/0268101 A1 | 10/2010 | Sugo | |
| 2010/0268518 A1 | 10/2010 | Sugo | |
| 2010/0298689 A1 | 11/2010 | Wang | |
| 2010/0324388 A1 | 12/2010 | Moon et al. | |
| 2010/0324431 A1 | 12/2010 | Addison et al. | |
| 2010/0324827 A1 | 12/2010 | Addison et al. | |
| 2011/0009754 A1* | 1/2011 | Wenzel ................. G03F 7/0002 600/485 |
| 2011/0009755 A1 | 1/2011 | Wenzel et al. | |
| 2011/0026784 A1 | 2/2011 | Van Slyke et al. | |

(56) References Cited

U.S. PATENT DOCUMENTS

| | | | |
|---|---|---|---|
| 2011/0034813 A1 | 2/2011 | Cohen et al. | |
| 2011/0040345 A1 | 2/2011 | Wenzel et al. | |
| 2011/0060234 A1 | 3/2011 | Zhou et al. | |
| 2011/0060531 A1 | 3/2011 | Sugo et al. | |
| 2011/0077532 A1 | 3/2011 | Kim et al. | |
| 2011/0087115 A1 | 4/2011 | Sackner et al. | |
| 2011/0098112 A1 | 4/2011 | LeBoeuf et al. | |
| 2011/0098546 A1 | 4/2011 | Farazi et al. | |
| 2011/0105918 A1 | 5/2011 | Fortin et al. | |
| 2011/0144711 A1* | 6/2011 | Bornzin | A61N 1/3686 607/18 |
| 2011/0172504 A1 | 7/2011 | Wegerich | |
| 2011/0196245 A1 | 8/2011 | Poupko et al. | |
| 2011/0209915 A1 | 9/2011 | Telfort et al. | |
| 2011/0224564 A1 | 9/2011 | Moon et al. | |
| 2011/0270097 A1 | 11/2011 | Aboy et al. | |
| 2011/0301436 A1 | 12/2011 | Teixeira | |
| 2012/0022350 A1 | 1/2012 | Teixeira | |
| 2012/0029320 A1 | 2/2012 | Watson et al. | |
| 2012/0029361 A1 | 2/2012 | Addison et al. | |
| 2012/0029363 A1 | 2/2012 | Lund | |
| 2012/0046557 A1 | 2/2012 | Kiani | |
| 2012/0053433 A1 | 3/2012 | Chamoun et al. | |
| 2012/0053469 A1 | 3/2012 | Melker | |
| 2012/0065485 A1 | 3/2012 | Benni et al. | |
| 2012/0065527 A1 | 3/2012 | Gill et al. | |
| 2012/0065528 A1 | 3/2012 | Gill et al. | |
| 2012/0078069 A1 | 3/2012 | Melker | |
| 2012/0109018 A1 | 5/2012 | Gertner et al. | |
| 2012/0136261 A1 | 5/2012 | Sethi et al. | |
| 2012/0172723 A1 | 7/2012 | Gertner | |
| 2012/0172732 A1 | 7/2012 | Meyer, Jr. | |
| 2012/0259235 A1 | 10/2012 | Addison et al. | |
| 2014/0303509 A1* | 10/2014 | Campbell | A61B 5/02007 600/485 |

FOREIGN PATENT DOCUMENTS

| | | |
|---|---|---|
| EP | 1443856 A2 | 8/2004 |
| EP | 1769737 A1 | 4/2007 |
| EP | 1884189 A1 | 2/2008 |
| EP | 2047794 A1 | 4/2009 |
| EP | 2217140 A1 | 8/2010 |
| EP | 2281508 A1 | 2/2011 |
| WO | 91/13589 A1 | 9/1991 |
| WO | 94/14372 A1 | 7/1994 |
| WO | 97/47236 A1 | 12/1997 |
| WO | 98/41279 A1 | 9/1998 |
| WO | 98/51212 A1 | 11/1998 |
| WO | 99/53834 A1 | 10/1999 |
| WO | 02/03076 A2 | 1/2002 |
| WO | 03/000125 A1 | 1/2003 |
| WO | 03/039326 A2 | 5/2003 |
| WO | 03/082099 A1 | 10/2003 |
| WO | 2004/071292 A1 | 8/2004 |
| WO | 2004/075746 A2 | 9/2004 |
| WO | 2005/055825 A1 | 6/2005 |
| WO | 2006/100676 A2 | 9/2006 |
| WO | 2007/109065 A1 | 9/2007 |
| WO | 2008/094598 A2 | 8/2008 |
| WO | 2008/144404 A1 | 11/2008 |
| WO | 2008/144525 A1 | 11/2008 |
| WO | 2009/009761 A1 | 1/2009 |
| WO | 2009/014420 A1 | 1/2009 |
| WO | 2009101140 A1 | 8/2009 |
| WO | 2010/001231 A2 | 1/2010 |
| WO | 2010045556 A2 | 4/2010 |
| WO | 2011/080190 A1 | 7/2010 |
| WO | 2010/096475 A1 | 8/2010 |
| WO | 2010096475 A1 | 8/2010 |
| WO | 2010/111073 A1 | 9/2010 |
| WO | 2010/124034 A2 | 10/2010 |
| WO | 2010/146326 A1 | 12/2010 |
| WO | 2010/146327 A1 | 12/2010 |
| WO | 2011/047211 A1 | 4/2011 |
| WO | 2011/050066 A2 | 4/2011 |
| WO | 2011/060220 A1 | 5/2011 |
| WO | 2011051822 A1 | 5/2011 |
| WO | 2011/077294 A1 | 6/2011 |
| WO | 2011/080194 A1 | 7/2011 |
| WO | 2011/087927 A1 | 7/2011 |
| WO | 2011/089488 A1 | 7/2011 |
| WO | 2012/009350 A1 | 1/2012 |
| WO | 2012/014065 A1 | 2/2012 |
| WO | 2012/015426 A1 | 2/2012 |
| WO | 2012/027613 A1 | 3/2012 |
| WO | 2012/032413 A2 | 3/2012 |
| WO | 2012/032536 A2 | 3/2012 |
| WO | 2012/052926 A2 | 4/2012 |
| WO | 2012/075322 A2 | 6/2012 |
| WO | 2012/076957 A1 | 6/2012 |

OTHER PUBLICATIONS

Elgendi, "On the Analysis of Fingertip Photoplethysmogram Signals," Current Cardiology Reviews, vol. 8, No. 1, Feb. 2012, pp. 14-25.

Sheinfeld et al., "Photoacoustic thermal diffusion flowmetry," Biomedical Optics Express, vol. 3, No. 4, Apr. 2012, pp. 800-813.

Moody et al., "Derivation of Respiratory Signals from Multi-lead ECGS," IEEE Computer Society Press, Computers in Cardiology, 1985 (Applicant points out, in accordance with MPEP 609.04(a), that the year of publication, 1985, is sufficiently earlier than the effective U.S. filing date, so that the particular month of publication is not in issue), 9 pp.

Allen, "Photophlethsmograptly and its application in clinical physiological measurement," IOP Publishing LTD., Physiological Measurement, vol. 28, No. 3, Feb. 20, 2007, 39 pp.

Zaja,"Venous Oximetry," Signa Vitae, vol. 2, No. 1, 2007 (Applicant points out, in accordance with MPEP 609.04(a), that the year of publication, 2007, is sufficiently earlier than the effective U.S. filing date, so that the particular month of publication is not in issue), pp. 6-10.

Hoffman, "Near-Infrared Spectrometry (NIRS) and Venous-side Monitoring of the Circulation," Children's Hospital and Medical College of Wisconsin, 2011 (Applicant points out, in accordance with MPEP 609.04(a), that the year of publication, 2011, is sufficiently earlier than the effective U.S. filing date, so that the particular month of publication is not in issue), 8 pp.

Natalani et al.,"Variations in Arterial Blood Pressure and Photoplethysmography During Mechanical Ventilation," Technology, Computing, and Simulation, vol. 103, No. 5, Nov. 2006, 7 pp.

Gonzalez et al., "A Computer Based Photoplethysmographic Vascular Analyzer Through Derivatives," Computers in Cardiology, vol. 35, Oct. 2008, 4 pp.

Millasseau et al., "Noninvasive Assessment of the Digital Volume Pulse: Comparison with the Peripheral Pressure Pulse," Journal of the American Heart Association, Hypertension, vol. 36, Jun. 26, 2000, 6 pp.

Poon, "Non-Invasive Estimation of Cardiac Output from Finger Photoplethysmogram Based of Windkessel Model," Bulletin of Advance Technology Research, vol. 4, No. 6, Jun. 2010, 4 pp.

Yoon et al., "Non-constrained Blood Pressure Monitoring Using ECG and PPG for Personal Healthcare," Journal of Medical Systems, vol. 33, Issue 4, Aug. 2009, pp. 261-266.

Vogel et al., "How to measure heat rate?", European Journal of Clinical Pharmacology, vol. 60, Aug. 5, 2004, pp. 461-466.

Fox et al., "Resting Heart Rate in Cardiovascular Disease," Elsevier, Journal of the American College of Cardiology, vol. 50, No. 9, Aug. 28, 2007, pp. 823-830.

Nauman, "Why measure resting heat rate?", Tidsskriftet Den Norske Legeforening, Issue 11, Jun. 12, 2012, 1 pp.

Marcinkevics et al., "The shape and dimensions of photoplethysmographic pulse waves: a measurement repeatability study," Acta Universitatis Latviensis, vol. 753, Biology, 2009 (Applicant points out, in accordance with MPEP 609.04(a), that the year

(56) References Cited

OTHER PUBLICATIONS of publication, 2009, is sufficiently earlier than the effective U.S. filing date, so that the particular month of publication is not in issue), pp. 99-106.

Selvavaj et al., "Monitoring of Reactive Hyperemia Using Photoplethysmographic Pulse Amplitude and Transit time," Journal of Clinical Monitoring and Computing, vol. 23, Issue 5, Oct. 2009, pp. 315-322.

Sheinfeld, et al., "Flow dependent photothermal modulation of the photoacoustic response," Photonos Plus Ultrasound: Imaging and Sensing, Feb. 2012.

Cannesson et al., "Relation between respiratory variations in pulse oximetry plethysmographic waveform amplitude and arterial pulse pressure in ventilated patients," Critical Care, vol. 9, No. 5, Aug. 23, 2005, 7 pp.

Chandler et al., "Pulse oximeter plethysmograph variation and its relationship to the arterial waveform in mechanically ventilated childer," Journal of Clinical Monitoring and Computing, vol. 23, Mar. 10, 2012, 7 pp.

Prosecution History from U.S. Appl. No. 13/609,566, dated Aug. 8, 2013 through Sep. 17, 2015, 107 pp.

Prosecution History from U.S. Appl. No. 14/977,301, dated Dec. 21, 2015 through Apr. 22, 2019, 130 pp.

Ishihara et al., "A New Non-lnvasive Continous Cardiac Output Trend Solely Utilizing Routine Cardiovascular Monitors," Journal of Clinical Monitoring and Computing, vol. 18, Dec. 2004, 8 pp.

Sugo et al., "A novel continuous cardiac output monitor based on pulse wave transit time," citing Abstract only, 2010 Annual International Conference IEEE Engineering in Medicine and Biology, IEEE, Aug. 2010.

\* cited by examiner

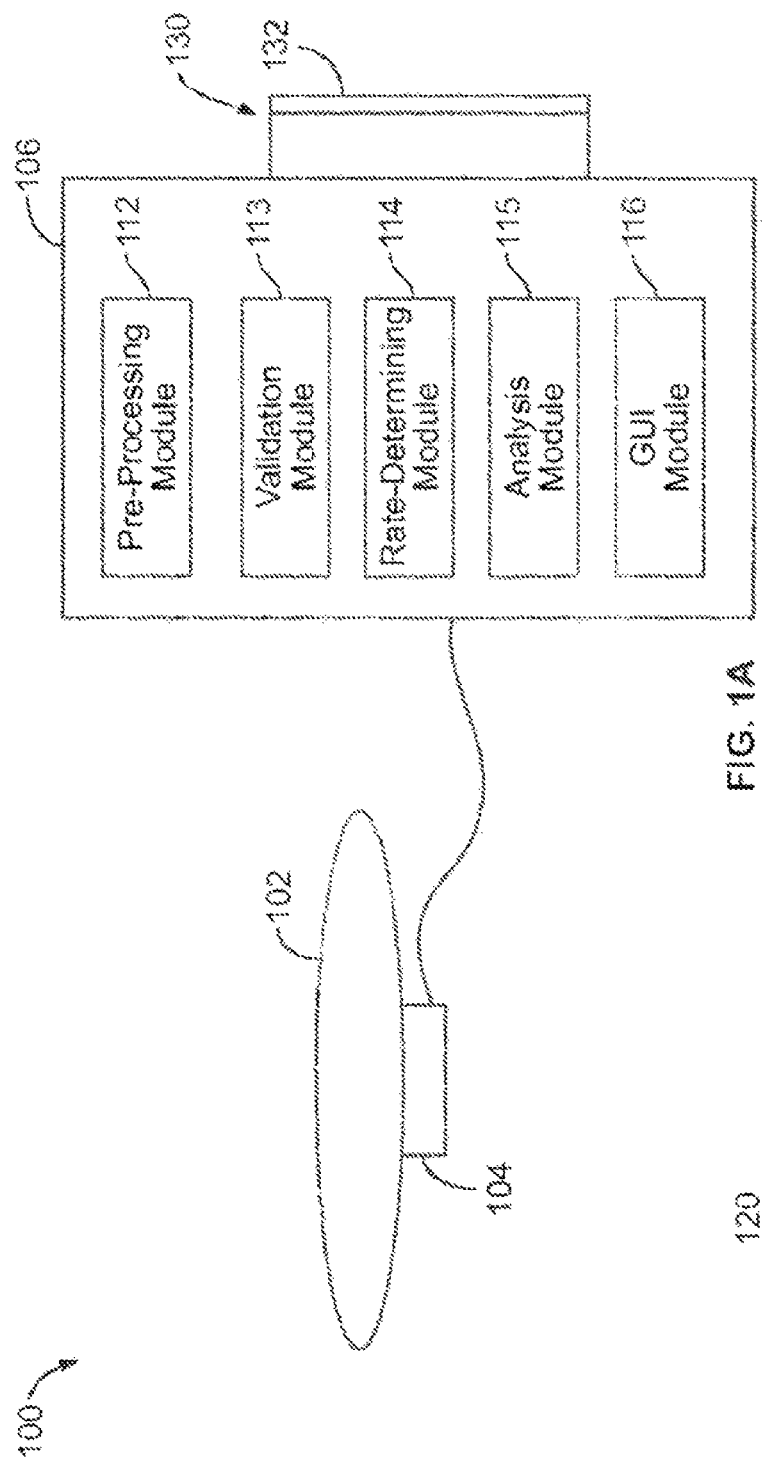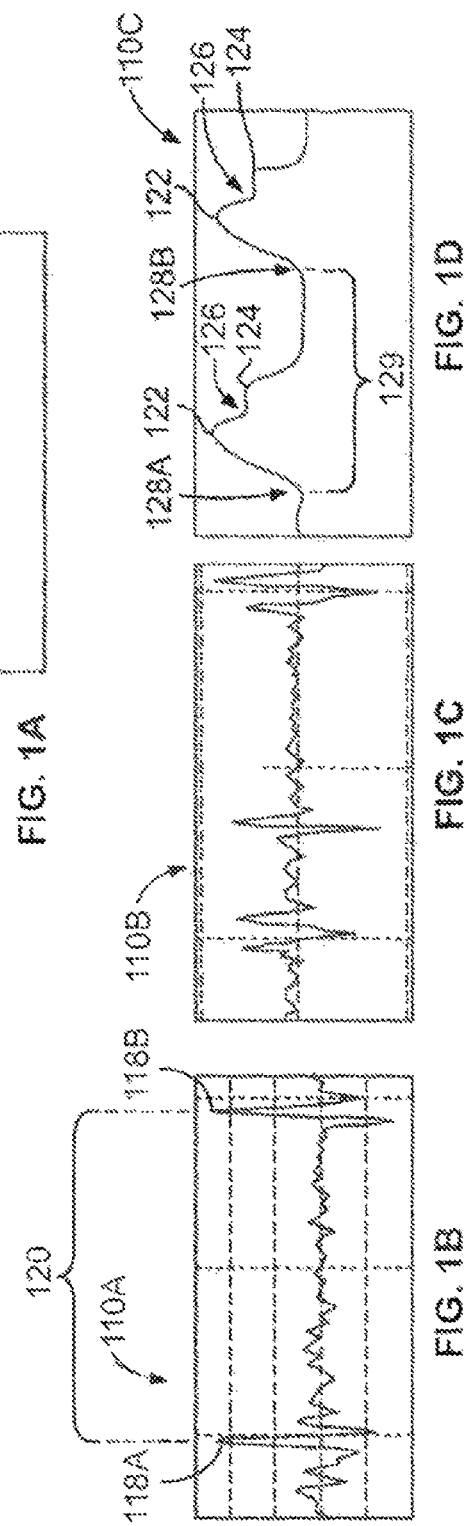

SYSTEM AND METHOD FOR DETERMINING STROKE VOLUME OF A PATIENT

This application is a continuation of U.S. patent application Ser. No. 14/977,301, which was filed on Dec. 21, 2015, is entitled, "SYSTEM AND METHOD FOR DETERMINING STROKE VOLUME OF PATIENT," and issued as U.S. Pat. No. 10,448,851 on Oct. 22, 2019 and is a divisional of U.S. patent application Ser. No. 13/609,566, which was filed on Sep. 11, 2012, is entitled, "SYSTEM AND METHOD FOR DETERMINING STROKE VOLUME OF PATIENT," and issued as U.S. Pat. No. 9,241,646 on Jan. 26, 2016. The entire content of each of U.S. patent application Ser. No. 14/977,301 and U.S. patent application Ser. No. 13/609,566 is incorporated herein by reference.

BACKGROUND

Embodiments of the present disclosure generally relate to physiological signal processing and, more particularly, to processing physiological signals to determine a stroke volume or cardiac output of a patient. In cardiovascular physiology, stroke volume (SV) is the volume of blood pumped from one ventricle of the heart with each beat. SV is calculated using measurements of ventricle volumes from an echocardiogram (ECG) and subtracting the volume of the blood in the ventricle at the end of a beat (end-systolic volume) from the volume of blood just prior to the beat (called end-diastolic volume). Stroke volume is an important determinant of cardiac output, which is the product of stroke volume and heart rate. Because stroke volume decreases in certain conditions and disease states, stroke volume itself correlates with cardiac function.

Systems and methods have been used to measure stroke volume. For example, photoplethysmogram (PPG) systems have been used in connection with ECG systems to aid in determining SV by measuring pulse transit times from the pulse measurement by the ECG system and the pulse measurement by the PPG system. The PPG system performs a non-invasive, optical measurement that may be used to detect changes in blood volume within tissue, such as skin, of an individual.

SUMMARY

Certain embodiments provide a PPG system for determining a stroke volume of a patient. The PPG system may include a PPG sensor configured to be secured to an anatomical portion of the patient. The PPG sensor is configured to sense a physiological characteristic of the patient. The PPG system may include a monitor operatively connected to the PPG sensor. The monitor receives a PPG signal from the PPG sensor. The monitor includes a pulse trending module configured to determine a slope transit time of an upslope of a primary peak of the PPG signal. The pulse trending module configured to determine a stroke volume of the patient as a function of the slops transit time. The PPG system may include a monitor that displays an output of the stroke volume on a display.

Optionally, the slope transit time may be calculated based upon a unit amplitude of the pulse. The slope transit time may be calculated by the pulse trending module as a temporal gradient of the PPG signal. The slope transit time may be calculated by the pulse trending module as an inverse of a gradient of the upslope of the primary peak of the PPG signal.

The PPG signal may form a PPG waveform. The pulse trending module may analyze a contour of the PPG waveform along the upslope of the primary peak to identify a gradient of the contour per unit amplitude. The pulse trending module may calculate the slope transit time as the inverse of the gradient. The pulse trending module may analyze a contour of the PPG waveform along the upslope of the primary peak to identify a temporal gradient of the contour per unit amplitude. The pulse trending module may calculate the slope transit time as a function of the temporal gradient.

The pulse trending module may analyze a contour of the PPG waveform along the upslope of the primary peak to identify at least one waveform characteristic thereof. The waveform characteristic may include at least one of an amplitude (A) of the contour, a gradient (m) of the contour and a temporal gradient (k) of the contour. The pulse trending module may calculate the stroke volume based upon at least one of the ratios of m=A/STT, k=1/m and k=STT.

The pulse trending module may calculate stroke volume based upon empirically determined constants. The pulse trending module may use a calibration constant to determine the stroke volume.

Certain embodiments provide a PPG system for determining a stroke volume of a patient. The PPG system may Include a PPG sensor configured to be secured to an anatomical portion of the patient to sense a physiological characteristic of the patient and generate a PPG signal. The PPG signal may have a primary peak, a trailing peak and a dicrotic notch for each pulse. The PPG system may include a monitor operatively connected to the PPG sensor. The monitor receives the PPG signal from the PPG sensor. The monitor includes a pulse trending module configured to determine waveform characteristics of an upslope of the primary peak of the PPG signal. The waveform characteristics may include an amplitude a gradient and a slope transit time of the PPG signal. The pulse trending module may be configured to determine a stroke volume as a function of the waveform characteristics of the upslope of the primary peak of the PPG signal.

Certain embodiments provide a method of determining a stroke volume of a patient from a PPG system. The method may include securing a PPG sensor to an anatomical portion of the patient, sensing a physiological characteristic of the patient with the PPG sensor and receiving a PPG signal from the sensor at a monitor. The monitor includes a pulse trending module. The method includes analyzing the PPG signal at the pulse trending module to determine a slope transit time of an upslope of a primary peak of the PPG signal. The method includes calculating a stroke volume at the pulse trending module of the patient based on the slope transit time of the upslope of the primary peak of the PPG signal.

The analyzing operation may include correlating the slope transit time of the upslope of the primary peak of the PPG signal to a slope transit time of an initial pressure wave. The analyzing operation may include analyzing a contour of the PPG waveform along the upslope of the primary peak to identify at least one waveform characteristic thereof, the waveform characteristic including at least one of an amplitude (A) of the contour, a gradient (m) of the contour and a temporal gradient (k) of the contour. The pulse trending module may calculate the slope transit time based upon at least one of the ratios of A/STT, k=1/m and k=STT.

The correlating operation may include calculating the slope transit time of the initial pressure wave as a function of effects of reflected waves of previous pulses based on at least one of wave periods, pulse periods, pulse transit times, and shapes of the previous waveforms.

The calculating operation may include calculating the stroke volume based upon the slope transit time and empirically determined constants.

Certain embodiments provide a tangible and non-transitory computer readable medium that includes one or more sets of instructions configured to direct a computer to receive a physiological signal from a sensor secured to an anatomical portion of a patient, determine a slope transit time of an upslope of a primary peek of the PPG signal, and calculate e stroke volume of the patient based on the slope transit time of the upslope of the primary peak of the PPG signal.

Embodiments of the present disclosure allow for quick and simple determination of stroke volume through analysis of a PPG signal. The PPG signal may be obtained from a single pleth-only system. In contrast to previous systems and methods, embodiments may not require multiple PPG sensors at multiple locations on the patient to determine pulse transit times for calculating stroke volume, in contrast to previous systems and methods, embodiments may not require another type of monitoring system such as an ECG system for measuring physiological conditions of the patient for use in calculations for the stroke volume. Moreover, embodiments may be used to measure temporal components of the PPG waveform that are independent of pulse transit times, respiratory effects and the like.

Certain embodiments may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

FIG. 1A illustrates a simplified block diagram of a system configured to determine a physiological parameter of a patient, according to an embodiment.

FIG. 1B illustrates an electrocardiogram (EGG) waveform of the patient, according to an embodiment.

FIG. 1C illustrates a phonocardiogram (PCG) waveform of the patient, according to an embodiment.

FIG. 1D illustrates a photoplethysmogram (PPG) waveform of the patient, according to an embodiment.

FIG. 6 illustrates a pulse waveform of a PPG signal, according to an embodiment.

DETAILED DESCRIPTION

Figure 2:
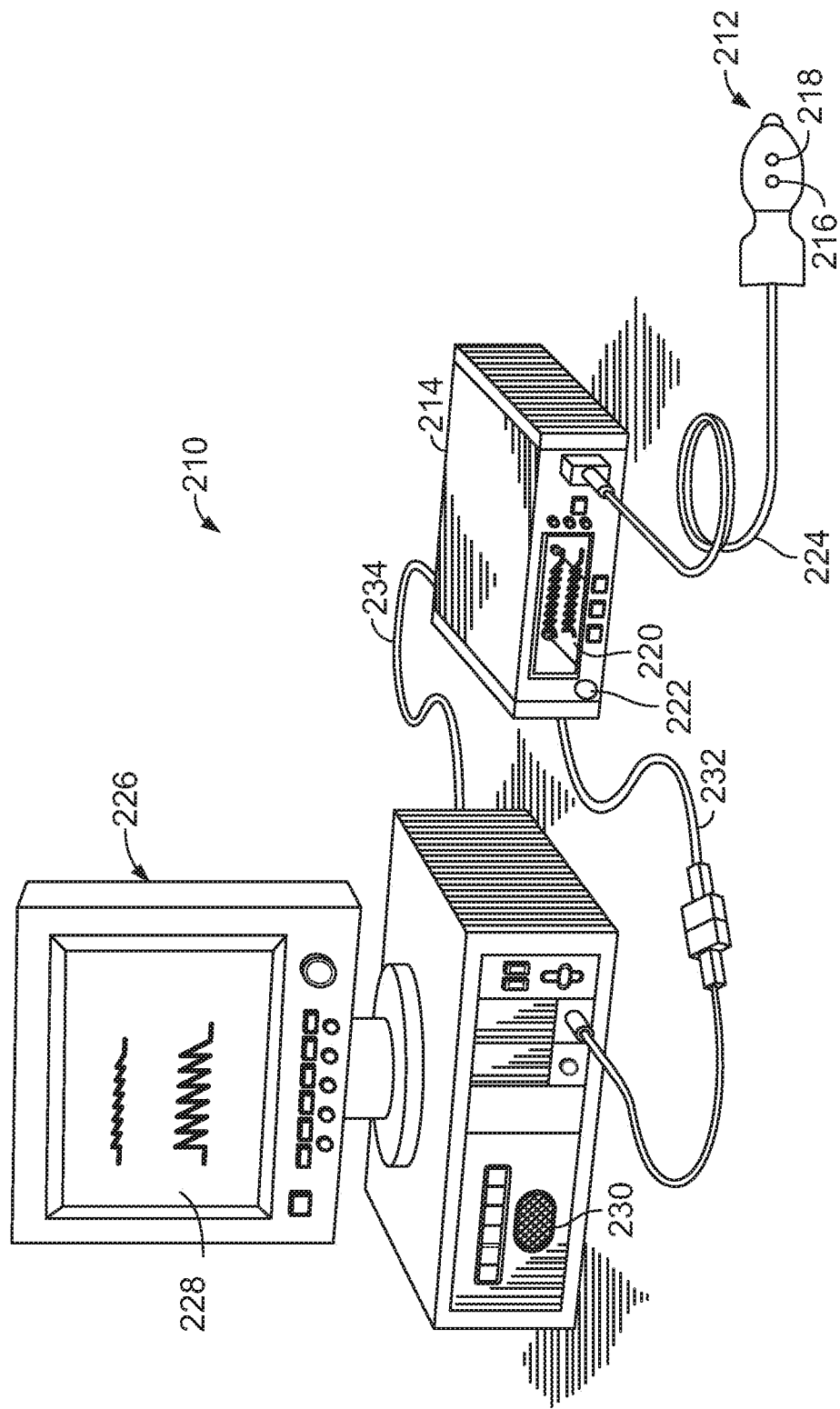
FIG. 2 illustrates an isometric view of a PPG system, according to an embodiment.

FIG. 1A illustrates a simplified block diagram of a system 100 configured to determine a physiological parameter of a patient 102. The system 100 is configured to acquire physiological signals (or biosignals) from the patient 102 and analyze the physiological signals to determine a physiological parameter, such as a stroke volume (SV) and/or a cardiac output (CO) of the patient 102. The SV is the volume of blood leaving the heart in a given contraction. The CO is the volume of blood being pumped by the heart, and is a function of SV and a heart rate (HR) of the patient 102. The physiological signals are indicative of phenomena occurring in the patient. For example, the physiological signals may describe cardiac activity in which the heart undergoes a number of cardiac cycles (e.g., heart beats). The physiological signals may be electrical, optical, and/or acoustical signals.

The system 100 may include a sensor 104 that is configured to detect one or more types of physiological signals. By way of example, the system 100 may include an electrocardiogram (BCG) system that detects electrical signals corresponding to muscle excitation of the heart. In such cases, the sensor 104 may include a plurality of electrodes that are coupled to different anatomical locations of the patient 102 (e.g., chest, wrists, and/or erodes). FIG. 1B illustrates, according to an embodiment, a representative ECO waveform 110A based on the ECG signals acquired by the electrode-sensor 104.

As another example, the system 100 may include a phonocardiogram (PCG) system that detects sounds that may be caused by the closing of heart valves. In such cases, the sensor 104 may include one or more microphones that are coupled to the patient 102. FIG. 1C illustrates, according to an embodiment, a representative PCG waveform 110B based on the PCG signals acquired by the microphone-sensor 104. In alternative embodiments, the system 100 includes an ultrasound system configured to detect heart beats from the patient 102.

In certain embodiments, the system 100 includes a photoplethysmogram (PPG) system, which can measure changes in blood volume through an anatomical portion or location (e.g., a finger). A typical example of a PPG system is a pulse oximetry system although other PPG systems exist and may be used with embodiments described herein. The PPG-sensor 104 may include a probe having one or more light sources and one or more light detectors that are coupled to the patient 102. The fight sources) provide an incident light that is scattered, absorbed, reflected, and/or transmitted by the blood. The light detectors) detect an amount of light that may correspond to blood volume. For example, as the volume of blood increases at the anatomical location, the light is attenuated more and, as such, a smaller amount of light is detected. FIG. 1C illustrates, according to an embodiment, a representative PPG waveform 110C based on the PPG signals acquired by the PPG-sensor 104.

As shown in FIG. 1A, the system 100 may include a monitor (or computing system) 106 that includes one or more components for analyzing and/or processing the physiological signals. For example, the monitor 106 may include a pre-processing module 112, a validation module 113, a rate-determining module 114, an analysis module 115, and a graphical user interface (GUI) module 116. As used herein, a "module" may include hardware components (e.g., processor, controller), software components, or a combination thereof including any associated circuitry.

The pre-processing module 112 is configured to remove unwanted signal date (e.g., noise) from raw physiological signal data obtained from the individual 102. For example, raw PPG signals may include artifacts caused by motion of the patient relative to the light detector, instrumentation bias (e.g., bias by amplifiers used in the PPG system), powerline interference, low amplitude PPG signals, etc. Raw physiological signals from other types of monitoring systems, such as ECG and PCG systems, may also include unwanted noise. The pre-processing module 112 is configured to remove the noise to provide clearer and/or cleaner physiological signals to the other components of the system 100.

The validation module 113 is configured to analyze the physiological signals to identify valid heart beats and waveforms from the physiological signals. In some embodiments, the validation module 113 is part of the pre-processing module 112 or another module. The validation module 113 may analyze the physiological signals after the physiological signals have been processed. In some embodiments, the validation module 113 examines the physiological signals to identify one or more reference features in the physiological signals. For instance, a series of data points over time may provide waveforms, such as the waveforms 110A-110C. A reference feature may be an identifiable point, segment, or characteristic of the waveform (e.g., peak, trough (or foot), notch, slope of a designated segment threshold, etc.) that may be relied upon in analysis of the physiological signals. In many cases, a reference feature of a waveform corresponds to a known physiological activity (e.g., excitation of heart muscles, closure or opening of valves, maximum volume of blood at an anatomical location, etc.). The validation module 113 may examine the data points, or a select number of data points (e.g., a segment of the waveform), to confirm that the data points are caused by a designated event of a cardiac cycle and are not a result of noise or other unwanted event, such as when the sensor 104 is being adjusted. The data points associated with valid heart beats may then be used by a rate-determining module 114 to determine a heart rate signal. In some embodiments, the data points that are not identified as corresponding to heart beats may not be considered in subsequent analysis.

The rate-determining module 114 is configured to analyze the heart beats or, more specifically, the data points corresponding to the valid heart beats identified by the validation module 113 and determine a HR of the individual at a designated moment of time. For example, the HR may be calculated by analyzing time intervals between two of more heart beats or by analyzing portions of a waveform that corresponds to a single heart beat. By way of example only, when analyzing the physiological signals, the rate-determining module 114 may identify one or more reference features (e.g., points, segments, and/or characteristics that correspond to a waveform) that may be used to calculate HR. For example, in the EGG waveform 110A, the rate-determining module 114 may identify an R-wave peak 118 in each heart beat. A time interval 120 between the R-wave peaks 118A, 118B may be determined and divided by a unit of time to calculate the HR. For example, if the time interval is 0.90 seconds between the two R-wave peaks 118A, 118B, then the HR is 67 beats/minute.

Corresponding to each heart beat, the PPG waveform 1100 may include a systolic peak 122, a diastolic peak 124, and a dicrotic notch 126 that exists therebetween. In some cases, the diastolic peak is not a peak but instead a change in slope. To determine HR, the rate-determining module 114 may identify for each heart beat a reference point that exists at a foot 128 of the wave before the systolic peak 122. The HR may be determined in a similar manner as described above with respect to the EGG waveform by identifying a time interval 129 between the foot 128A and the foot 128B.

However, it should be noted that the above description is just exemplary and that many reference points and/or waveform segments may be analyzed and used to calculating a HR of an individual. Furthermore, the physiological signals may be processed in various manners to determine a HR. For example, a first derivative or second derivative of the PPG waveform may be used to locate certain reference data points m the PPG waveform. Such reference data points may be used for determining the heart rate or for determining other physiological parameters.

As will be described in greater detail below, the analysis module 115 is configured to identify data points from the physiological signals. The signal data points may be a limited number of data points from a series of data points. For example, the signal data points may correspond to a peak data point, a trough data point, a segment of data points that correspond to a slope of the waveform, and the like. To calculate a physiological parameter, such as the SV and/or CO, the analysis module 115 may use one or more of the data points to calculate the physiological parameter.

The system 100 may also include a user interface 130 that includes a display 132. The user interface 130 may include hardware, firmware, software, or a combination thereof that enables a user to directly or indirectly control operation of the system 100 and the various components thereof. The display 132 is configured to display one or more images, such as one or more of the waveforms 110A-110C. The display 132 may also be configured to show a representation of the physiological parameter, for example, a number representing the SV or the CO. In some embodiments, the user interface 130 may also include one or more input devices (not shown), such as a physical keyboard, mouse, touchpad, end/or touch-sensitive display. The user interface 130 may be operatively connected to the GUI module 116 and receive instructions from the GUI module 116 to display designated images on the display 132. The user interface 130 may also include a printer or other device for providing (e.g. printing) a report. The user interface 130 may also include an alarm or alert system.

There are many medical conditions in which SV and CO are relevant. For example, uncontrolled atrial fibrillation is a condition characterized by an abnormally rapid heart rate caused by unregulated firing of electrical pulses within the heart muscles. This rapid firing induces an elevated heart rate (known as tachycardia) while simultaneously preventing the ventricles from filling completely with blood before the next contraction. In this condition, the HR increases while SV decreases. As a result the CO (total volume of blood pumped to the body from the heart) can decrease during atrial fibrillation, leading to a decrease in blood pressure (BP).

Detecting a change in the SV, CO, HR and/or BP can alert medical providers to potentially dangerous patient conditions. Analyzing and/or processing the physiological signals to provide a representation of SV and/or CO on a display for a care provider may be more meaningful than merely monitoring BP and HR readings. A monitoring system that tracks and provides information relating to SV and/or CO for a care provider and indicates a patient status in response to calculated SV and/or CO provides a tool in patient diagnosis and treatment. The present disclosure relates to systems and methods for detecting SV and/or CO to determine patient status, and more particularly, relates to analyzing a trending nature of a waveform to determine SV and/or CO to alert a care provider to a patient condition. For example, the present disclosure relates to systems and methods that analyze a slope transit time of a PPG signal for determining SV and/or CO.

FIG. 2 illustrates an isometric view of a PPG system 210, according to an embodiment. The PPG system 210 may be used as part of the system 100 (shown in FIG. 1). While the system 210 is shown and described as a PPG system 210, the system may be various other types of physiological detection systems, such as an electrocardiogram system, a phonocardiogram system, and the like. The PPG system 210 may be a pulse oximetry system, for example. The system 210 may include a PPG sensor 212 and a PPG monitor 214. The PPG sensor 212 may include an emitter 216 configured to emit light into tissue of a patient. For example, the emitter 216 may be configured to emit light at two or more wavelengths into foe tissue of the patient. The PPG sensor 212 may also include a detector 218 that is configured to detect the emitted light from the emitter 216 that emanates from the tissue after passing through the tissue.

The system 210 may include a plurality of sensors forming a sensor array in place of the PPG sensor 212. Each of the sensors of the sensor array may be a complementary metal oxide semiconductor (CMOS) sensor, for example. Alternatively, each sensor of the array may be a charged coupled device (CCD) sensor, in another embodiment, the sensor array may include a combination of CMOS and CCD sensors. The CCD sensor may include a photoactive region and a transmission region configured to receive and transmit, while the CMOS sensor may include an integrated circuit having an array of pixel sensors. Each pixel may include a photodetector and an active amplifier.

The emitter 216 and the detector 218 may be configured to be located at opposite sides of a digit, such as a finger or toe, in which case the light that is emanating from the tissue passes completely through the digit. The emitter 216 and the detector 218 may be arranged so that light from the emitter 216 penetrates the tissue and is reflected by the tissue into the detector 218, such as a sensor designed to obtain pulse oximetry data.

The sensor 212 or sensor array may be operatively connected to and draw power from the monitor 214. Optionally, the sensor 212 may be wirelessly connected to the monitor 214 and include a battery or similar power supply (not shown). The monitor 214 may be configured to calculate physiological parameters based at least in part on data received from the sensor 212 relating to light emission and detection. Alternatively, the calculations may be performed by and within the sensor 212 and the result of the oximetry reading may be passed to the monitor 214. Additionally, the monitor 214 may include a display 220 configured to display the physiological parameters or other information about the system 210. The monitor 214 may also include a speaker 222 configured to provide an audible sound that may be used in various other embodiments, such as for example, sounding an audible alarm in the event that physiological parameters are outside a predefined normal range.

The sensor 212, or the sensor array, may be communicatively coupled to the monitor 214 via a cable 224. Alternatively, a wireless transmission device (not shown) or the like may be used instead of, or In addition to, the cable 224.

The system 210 may also include a multi-parameter workstation 226 operatively connected to the monitor 214. The workstation 226 may be or include a computing sub-system 230, such as standard computer hardware. The computing sub-system 230 may include one or more modules and control unite, such as processing devices that may include one or more microprocessors, microcontrollers, integrated circuits, memory, such as read-only and/or random access memory, and the like. The workstation 226 may include a display 228, such as a cathode ray tube display, a flat panel display, such as a liquid crystal display (LCD), light-emitting diode (LED) display, a plasma display, or any other type of monitor. The computing sub-system 230 of the workstation 226 may be configured to calculate physiological parameters and to show information from the monitor 214 and from other medical monitoring devices or systems (not shown) on the display 228. For example, the workstation 226 may be configured to display SV information, CO information, an estimate of a patient's blood oxygen saturation generated by the monitor 214 (referred to as an SpO2 measurement), pulse rate information from the monitor 214 and blood pressure from a blood pressure monitor (not shown) on the display 228.

The monitor 214 may be communicatively coupled to the workstation 226 via a cable 232 and/or 234 that is coupled to a sensor input port or a digital communications port, respectively and/or may communicate wirelessly with the workstation 226. Alternatively, the monitor 214 and the workstation 226 may be integrated as part of a common device. Additionally, the monitor 214 and/or workstation 228 may be coupled to a network to enable the sharing of information with servers or other workstations. The monitor 214 may be powered by a battery or by a conventional power source such as a wall outlet.

Figure 3:
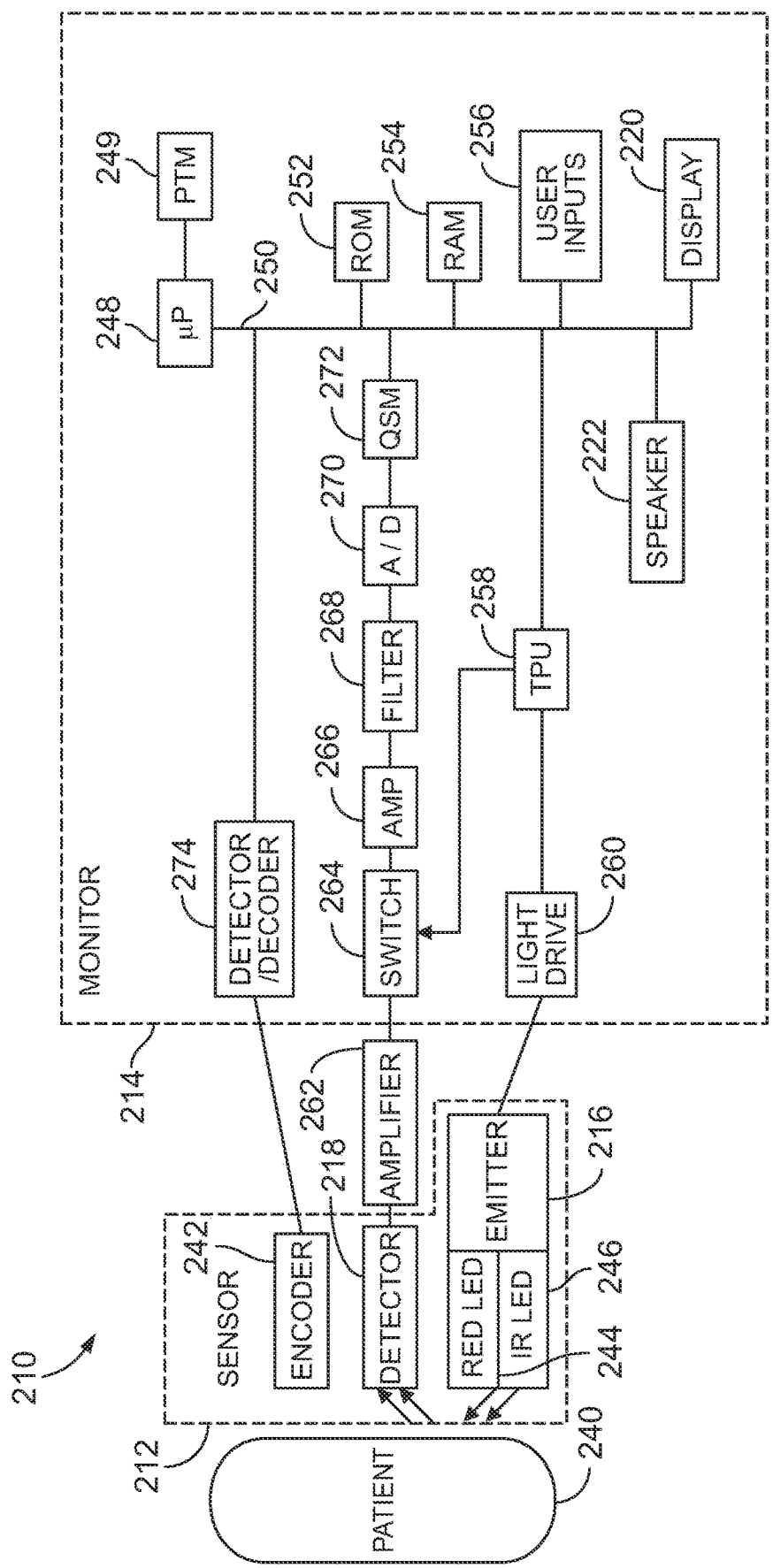
FIG. 3 illustrates a simplified block diagram of a PPG system, according to an embodiment.

FIG. 3 frustrates a simplified block diagram of the PPG system 210, according to an embodiment, when the PPG system 210 is a pulse oximetry system, the emitter 216 may be configured to emit at least two wavelengths of light (for example, red and infrared) into tissue 240 of a patient. Accordingly, the emitter 216 may include a red light-emitting light source such as a red light-emitting diode (LED) 244 and an infrared light-emitting light source such as an infrared LED 246 for emitting light into the tissue 240 at the wavelengths used to calculate the patient's physiological parameters. For example, the red wavelength may be between about 600 nm and about 700 nm, and the infrared wavelength may be between about 800 nm and about 1000 nm. In embodiments where a sensor array is used in place of single sensor, each sensor may be configured to emit a single wavelength. For example, a first sensor may emit a red light while a second sensor may emit an infrared light.

As discussed above, the PPG system 210 is described m terms of a pulse oximetry system. However, the PPG system 210 may be various other types of systems. For example, the PPG system 210 may be configured to emit more or less than two wavelengths of light into the tissue 240 of the patient. Further, the PPG system 210 may be configured to emit wavelengths of light other than red and infrared into the tissue 240. As used herein, the term "light" may refer to energy produced by radiative sources and may include one or more of ultrasound, radio, microwave, millimeter wave, infrared, visible, ultraviolet, gamma ray or X-ray electromagnetic radiation. The light may also include any wavelength within the radio, microwave, infrared, visible, ultraviolet or X-ray spectra, and that any suitable wavelength of electromagnetic radiation may be used with the system 210. The detector 218 may be configured to be specifically sensitive to the chosen targeted energy spectrum of the emitter 216.

The detector 218 may be configured to detect the intensity of light at the red and infrared wavelengths. Alternatively, each sensor in the array may be configured to detect an intensity of a single wavelength. In operation, light may enter the detector 218 after passing through the tissue 240. The detector 218 may convert the intensity of the received light into an electrical signal. The light intensity may be directly related to the absorbance and/or reflectance of light in the tissue 240. For example, when more light at a certain wavelength is absorbed or reflected, less light of that wavelength is received from the tissue by the detector 218. After converting the received light to an electrical signal, the detector 218 may send the signal to the monitor 214, which calculates physiological parameters based on the absorption of the red and infrared wavelengths in the tissue 240.

In an embodiment, an encoder 242 may store information about the sensor 212, such as sensor type (for example, whether the sensor is intended for placement on a forehead or digit) and the wavelengths of light emitted by the emitter 216. The stored information may be used by the monitor 214 to select appropriate algorithms, lookup tables and/or calibration coefficients stored in the monitor 214 for calculating physiological parameters of a patient. The encoder 242 may store or otherwise contain information specific to a patient, such as, for example, the patient's age, weight, and diagnosis. The information may allow the monitor 214 to determine, for example, patient-specific threshold ranges related to the patient's physiological parameter measurements, and to enable or disable additional physiological parameter algorithms. The encoder 242 may, for instance, be a coded resistor that stores values corresponding to the type of sensor 212 or the types of each sensor to the sensor array, the wavelengths of light emitted by emitter 216 on each sensor of the sensor array, and/or the patient's characteristics. Optionally, the encoder 242 may include a memory in which one or more of the following may be stored for communication to the monitor 214; the type of the sensor 212, the wavelengths of light emitted by emitter 216, the particular wavelength each sensor in the sensor array is monitoring, a signal threshold for each sensor to the sensor array, any other suitable information, or any combination thereof.

Signals from the detector 218 and the encoder 242 may be transmitted to the monitor 214. The monitor 214 may include a general-purpose control unit, such as a microprocessor 248 connected to an internal bus 250. The microprocessor 248 may be configured to execute software, which may include an operating system and one or more applications, as part of performing the functions described herein. A read-only memory (ROM) 252, a random access memory (RAM) 254, user inputs 256, the display 220, and the speaker 222 may also be operatively connected to the bus 250. The control unit and/or the microprocessor 248 may include a pulse trending module 249 that is configured to determine a trending nature, index or value of the PPG signals or waveform. In an embodiment, the pulse trending module 249 analyzes the PPG signal to determine a slope transit time of a segment of the PPG signal as a basis for determining the stroke volume of the patient. The pulse trending module 249 is configured to determine a stroke volume based on calculations, measurements or other information, data or signals received from the PPG sensor 212.

The RAM 254 and the ROM 252 are illustrated by way of example, and not limitation. Any suitable computer-readable media may be used in the system for data storage. Computer-readable media are configured to store information that may be interpreted by the microprocessor 248. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The monitor 214 may also include a time processing unit (TPU) 258 configured to provide timing control signals to a light drive circuitry 260, which may control when the emitter 216 is illuminated and multiplexed timing for the red LED 244 and the infrared LED 246. The TPU 258 may also control the gating-in of signals from the detector 218 through an amplifier 262 and a switching circuit 264. The signals are sampled at the proper time, depending upon which light source is illuminated. The received signal from the detector 218 may be passed through an amplifier 266, a tow pass filter 268, and an analog-to-digital converter 270. The digital data may then be stored in a queued serial module (QSM) 272 (or buffer) for later downloading to RAM 254 as GSM 272 fills up. In an embodiment, there may be multiple separate parallel paths having amplifier 266, filter 268, and A/D converter 270 for multiple light wavelengths or spectra received.

The microprocessor 248 may be configured to determine the patient's physiological parameters, such as SV, CO, SpO2, pulse rate, and the like, using various algorithms and/or look-up tables based on the values) of the received signals and/or data corresponding to the light received by the detector 218. The signals corresponding to information about a patient, and regarding the intensity of light emanating from the tissue 240 over time, may be transmitted from the encoder 242 to a decoder 274. The transmitted signals may include, for example, encoded information relating to patient characteristics. The decoder 274 may translate the signals to enable the microprocessor 248 to determine the thresholds based on algorithms or look-up tables stored in the ROM 252. The user inputs 256 may be used to enter information about the patient, such as age, weight, height, diagnosis, medications, treatments, and so forth. The display 220 may show a list of values that may generally apply to the patient, such as, for example, age ranges or medication families, which the user may select using the user inputs 266.

As noted, the PPG system 210 may be a pulse oximetry system. A pulse oximeter is a medical device that may determine oxygen saturation of blood. The pulse oximeter may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of a patient. Pulse oximeters typically measure and display various blood flow characteristics including, but not limited to, the oxygen saturation of hemoglobin in arterial blood.

A pulse oximeter may include a light sensor, similar to the sensor 212, that is placed at a site on a patient, typically a fingertip, toe, forehead or earlobe, or in the case of a neonate, across a foot. The pulse oximeter may pass light using a light source through blood perfused tissue and photoelectrically sense the absorption of light in the tissue. For example, the pulse oximeter may measure the intensity of light that is received at the light sensor as a function of time. A signal representing light intensity versus time or a mathematical manipulation of this signal (for example, a scaled version thereof, a log taken thereof, a scaled version of a log taken thereof, and/or the like) may be referred to m the photoplethysmogram (PPG) signal. In addition, the term "PPG signal" m used herein, may also refer to an absorption signal (for example, representing the amount of light absorbed by the tissue) or any suitable mathematical manipulation thereof. The light intensity or the amount of light absorbed may then be used to calculate the slope transit time of the pulse, the amount of the blood constituent (for example, oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related tight absorption. Red and infrared wavelengths may be used because it has been observed that highly oxygenated blood will absorb relatively less red fight and more infrared light than blood with lower oxygen saturation. By comparing the intensities of two wavelengths at different points in the pulse cycle, it is possible to estimate the blood oxygen saturation of hemoglobin in arterial blood.

Stroke volume may correlate with cardiac health and other physiological parameters important in patient care, such as fluid responsiveness. Fluid responsiveness relates to the volume of fluid, such as blood, in the arteries, veins, and vasculature of an individual. In general, fluid responsiveness may include a measurement of the response of stroke volume, the volume of blood passing out of the heart with each heartbeat, to venous return, the volume of blood entering the heart with each heartbeat, caused by the clinical administration of fluid into the vasculature, such as through an intravenous inaction. With each heartbeat, a certain amount of blood is pumped out of the heart. The more blood that fills the heart, the more blood the heart can pump out with each heartbeat. If blood volume is too low, the heart may not fully fill with blood. Therefore, the heart may not pump out as much blood with each heartbeat. Consequently, low blood volume may load to tow blood pressure, and organs and tissues may not receive enough blood to optimally and/or properly function. Monitoring stroke volume and fluid responsiveness allows a physician to determine whether additional fluid should be provided to a patient, such as through an intravenous fluid injection. In short, fluid responsiveness represents a prediction of whether or not additional intravenous fluid may improve blood flow within a patient. Fluid responsiveness may be viewed as a response of a heart in relation to overall fluid within a patient.

Stroke volume may be monitored in, for example, critically-ill patients because fluid administration plays an important role in optimizing cardiac output and oxygen delivery to organs and tissues. However, clinicians need to balance central blood volume depletion and volume overloading. Critically-ill patients are generally at greater risk for volume depletion and severe hypotension is a common life-threatening condition in critically-ill patients. Conversely, administering too much fluid may induce life-threatening adverse effects, such as volume overload, systemic and pulmonary edema, and increased tissue hypoxia. Therefore, obtaining reliable information and parameters that aid clinicians in fluid management decisions may help improve patient outcomes.

Figure 4:
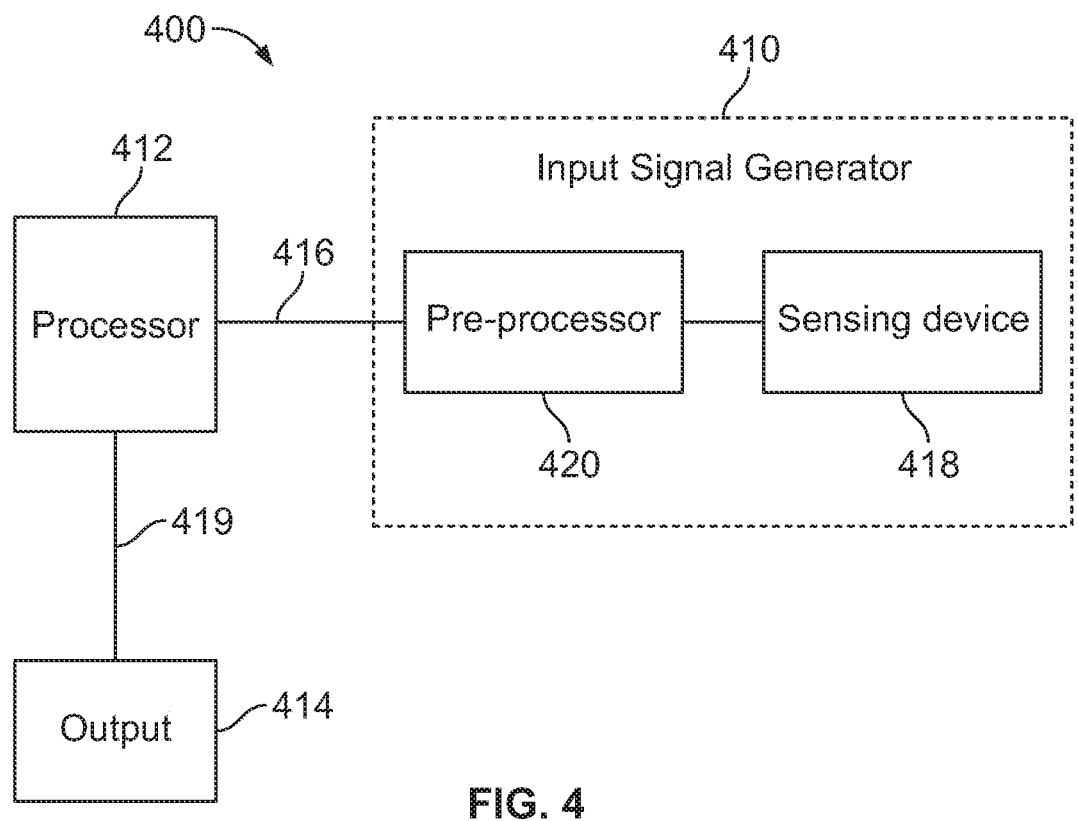
FIG. 4 is an illustrative processing system in accordance with an embodiment.

FIG. 4 is an illustrative processing system 400 in accordance with an embodiment. In an embodiment, an input signal generator 410 generates an input signal 416. The input signal generator 410 includes a pre-processor 420 coupled to a sensing device 418. It will be understood that the input signal generator 410 may include any suitable signal source, signal generating data, signal generating equipment, or any combination thereof to produce the signal 416. The signal 416 may be a single signal, or may be multiple signals transmitted over a single pathway or multiple pathways.

The pre-processor 420 may apply one or more signal processing techniques to the signal generated by the sensing device 418. For example, the pre-processor 420 may apply a pre-determined transformation to the signal provided by the sensing device 418 to produce an input signal 416 that can be appropriately interpreted by the processor 412. The pre-processor 420 may also perform any of the following operations to the signal provided by the sensing device 418; reshaping the signal for transmission; multiplexing the signal; modulating the signal onto carrier signals; compressing the signal; encoding the signal; and filtering the signal.

In the embodiment of FIG. 4, the signal 416 is coupled to the processor 412. The processor 412 may be any suitable software, firmware, and/or hardware, and/or combinations thereof for processing the signal 416. For example, the processor 412 may include one or more hardware processors (e.g., integrated circuits), one or more software modules, computer-readable media such as memory, firmware, or any combination thereof. The processor 412 may, for example, be a computer or may be one or more chips (i.e., Integrated circuits). The processor 412 may, for example, be configured of analog electronic components. The processor 412 may perform some or all of the calculations associated with the monitoring methods of the present disclosure. For example, the processor 412 may analyze the physiological signals, waveforms, and the like and compute pulse trending characteristics thereof to determine a stroke volume and/or cardiac output, as discussed further below. The processor 412 may also perform any suitable signal processing to filter the signal 418, such as any suitable band-pass filtering, adaptive filtering, closed-loop filtering, and/or any other suitable filtering, and/or any combination thereof. The processor 412 may also receive input signals from additional sources (not shown). For example, the processor 412 may receive an input signal containing information about the patient or treatments provided to the patient. These additional input signals may be used by the processor 412 in any of the calculations or operations it performs in accordance with the processing system 400.

The processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both, in an embodiment, the processor 412 may store physiological measurements or previously received data from the signal 416 in a memory device for later retrieval. The processor 412 may be coupled to a calibration device (not shown) that may generate or receive as input reference measurements for use in calibrating calculations.

The processor 412 is coupled to an output 414 through a patient status indicator signal 419, and may be coupled through additional signal pathways not shown. The output 414 may be any suitable output device such as, for example, one or more medical devices (e.g., a medical monitor that displays various physiological parameters, a medical alarm, or any other suitable medical device that either displays physiological parameters or uses the output of the processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof. In an embodiment, the patient status indicator signal 419 induces at least one of an identification of a medical condition of the patient; an alert; a current stroke volume measurement; a current cardiac output measurement; a current HR measurement; a current BP measurement; another current physiological measurement; an estimated patient status; and an estimated patient outcome. In some embodiments, the patient status indicator signal 419 will be stored in a memory device or recorded m another physical form for future, further analysis.

It will be understood that the system 400 may be incorporated into the system 100 (shown in FIG. 1) and/or the system 210 (shown in FIGS. 2 and 3) in which, for example, the input signal generator 410 may be implemented as parts of the sensor 212 and/or the monitor 214 and the processor 412 may be implemented as part of the monitor 214, in some embodiments, portions of the system 400 may be configured to be portable. For example, all or a part of the system 400 may be, embedded in a small, compact object carried with or attached to the patient (e.g., a watch, other piece of jewelry, or cellular telephone). In such embodiments, a wireless transceiver (not shown) may also be included in the system 400 to enable wireless communication with other components of system 210. As such, the system 210 may be part of a fully portable and continuous monitoring solution.

Figure 5:
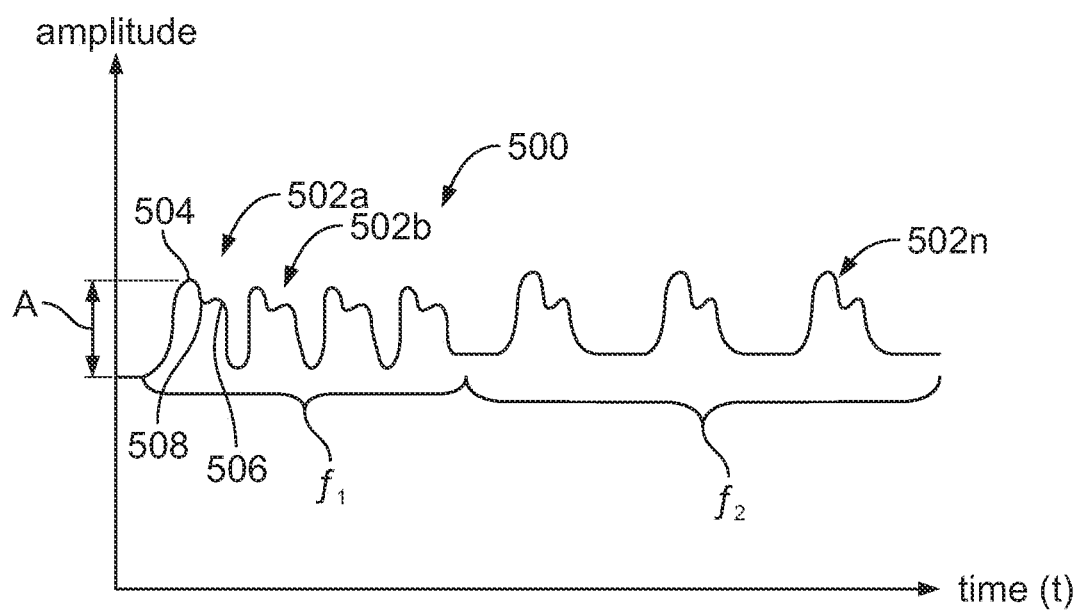

FIG. 5 illustrates a PPG signal 600 over time, according to an embodiment. The PPG signal 500 is an example of a physiological signal. However, embodiments may be used in relation to various other physiological signals, such as electrocardiogram signals, phonocardiogram signals, ultrasound signals, and the like. The PPG signal 500 may be determined, formed, and displayed as a waveform by the monitor 214 (shown in FIG. 2) that receives signal data from the PPG sensor 212 (shown in FIG. 2). For example, the monitor 214 may receive signals from the PPG sensor 212 positioned on a finger of a patient. The monitor 214 processes the received signals, and displays the resulting PPG signal 600 on the display 228 (shown in FIG. 2).

The PPG signal 500 may include a plurality of pulses 502a-502n over a predetermined time period. The time period may be a fixed time period, or the time period may be variable. Moreover, the time period may be a rolling time period, such as a 5 second rolling timeframe.

Each pulse 502a-502n may represent a single heartbeat and may include a pulse-transmitted or primary peak 504 separated from a pulse-reflected or trailing peak 506 by a dicrotic notch 508. The primary peak 504 represents a pressure wave generated from the heart to the point of detection, such as in a finger where the PPG sensor 212 is positioned. The trailing peak 506 represents a pressure wave that is reflected from the location proximate where the PPG sensor 212 is positioned back toward the heart. Characteristics of the primary peak 504 and/or the trailing peak 506 may be analyzed by the pulse trending module 249 (shown in FIG. 3) to calculate the stroke volume or other physiological parameters of the patient.

As shown in FIG. 5, each pulse 502a-502n has a particular amplitude A. For example, the pulse 502a has an amplitude A. The amplitudes A may differ with respect to one another. In general, the overall amplitude of the PPG signal 500 over time t may modulate. The pulse bending module 249 (shown in FIG. 3) of the monitor 214 may track and store the magnitude of the amplitude modulation of the PPG signal 500 over time t. Optionally, the pulse trending module 249 of the monitor 214 may track and store the magnitude of the amplitude of any number of the pulses 502a-502n for use in determining a stroke volume, cardiac output or other physiological parameter of the patient. For example, the pulse trending module 249 of the monitor 214 may use a single pulse 502a, analyze the single pulse to determine a trending nature of the waveform thereof, and calculate the stroke volume, cardiac output or other physiological parameter of the patient based on the single pulse 502a. Alternatively, the pulse trending module 249 may use multiple pulses 502a-502n, analyze the trending nature of the waveforms thereof, and calculate the stroke volume, cardiac output or other physiological parameter of the patient based upon a comparison of the amplitudes or other aspects of the waveforms of the pulses 502a-502n to calculate the stroke volume, cardiac output or other physiological parameter of the patient. Optionally, the pulse trending module 249 of the monitor 214 may determine an average modulation of the pulses 502a-502n over a time period t and use the average modulation to calculate the stroke volume, cardiac output or other physiological parameter of the patient.

As shown in FIG. 5, the frequency of the pulses 502a-502n may vary. For example, the frequency U of the pulses over a first period of time may vary from a frequency $f_2$ over a later period of time. The monitor 214 (shown m FIG. 2) may monitor and determine the frequencies $f_1$ and $f_2$. The frequency variation may be based upon respiration, blood pressure, heart rate, or other factors. The pulse trending module 249 of the monitor 214 may detect a magnitude of frequency modulation over a time period t. The pulse bending module 249 of the monitor 214 may use the frequency of the pulses, or any other temporal element of the pulses, to analyze the trending nature of the waveforms thereof, and calculate the stroke volume, cardiac output or other physiological parameter of the patient.

Figure 6:
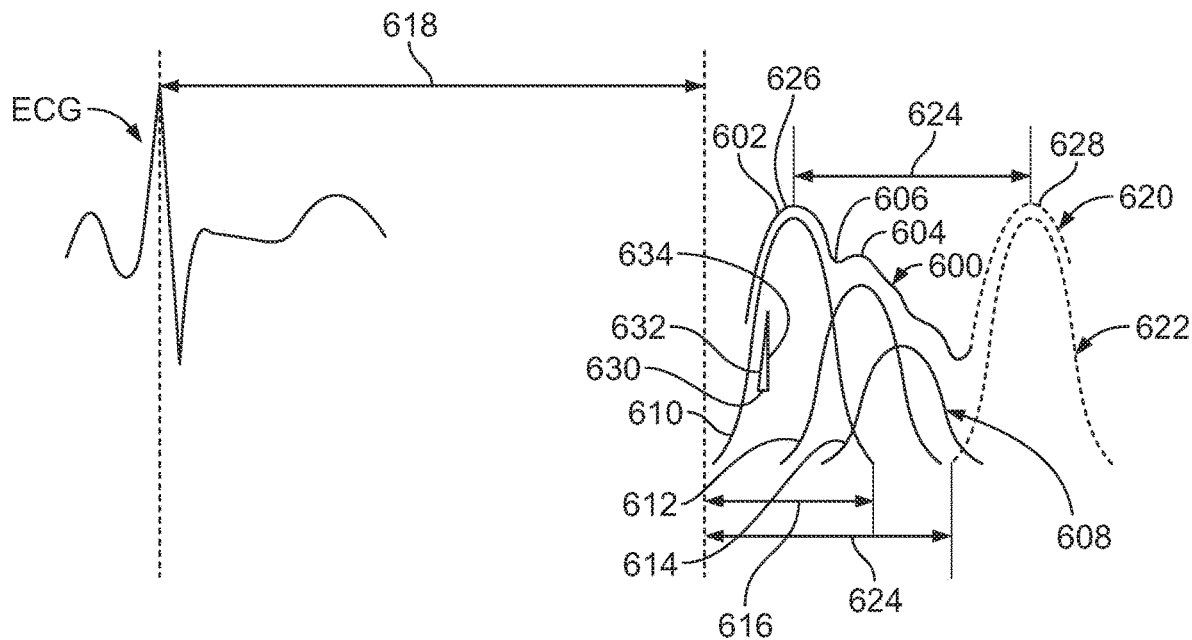
FIG. 6 illustrates a PPG signal over time, according to an embodiment.

FIG. 6 illustrates a pulse waveform 600 of a PPG signal, according to an embodiment while the pulse waveform 600 is described as a component of a PPG signal, the pulse waveform 600 may be a component of various other physiological signals. The pulse waveform 600 represents a single heartbeat and may include a primary peak 602 separated from a trailing peak 604 by a dicrotic notch 606.

The pulse waveform 600 is defined by a plurality of internal pulse components 608 of a given pulse. The internal pulse components 608 aggregate together, and may aggregate with internal pulse components of previous pulses) to define the pulse waveform 600. The internal pulse components 608 generally include an initial pressure wave 610 generated from the heart to the point of detection, such as in a finger where the PPG sensor 212 (shown in FIG. 2) is positioned, and a series of reflected pressure waves 612, 614 (any number of reflected waves may occur, while only two are illustrated in FIG. 6 as additional reflected waves have diminishing effects on the pulse waveform 600). The primary peak 602 is dominated by the initial pressure wave 610 (but may be affected by reflected waves of previous pulses as evidenced by the slight increase in amplitude of the primary peak 602 as compared to the initial pressure wave 610). The trailing peak 604 is defined mostly, if not entirely, by the reflected pressure waves 612, 614 that are reflected from the location proximate where the PPG sensor 212 is positioned back toward the heart.

Various waveform characteristics may be measured and/or calculated from the pulse waveform 60Q. The waveform characteristics may be used by the pulse trending module 249 (shown in FIG. 3) to calculate the stroke volume, cardiac output or other physiological parameter of the patient. For example, as described in further detail below, the pulse trending module 249 may utilize a wave period, a pulse period, a transit time, an amplitude, a peak, a temporal element, a gradient, a change in any of the waveform characteristics, and the like to calculate the stroke volume, cardiac output or other physiological parameter of the patient.

An internal wave period 616 is a measure of a temporal element of the initial pressure wave 610. For example, the internal wave period 618 may be indicative of a transit time of a given pulse. Optionally, the reflected pressure waves 612, 614 may have the same wave periods as the initial wave period. The wave period 618 may be affected by other physiological conditions of the patient, such as blood pressure, heart rate, respiration, and the like. The wave period 616 is variable depending on the physiological status of the patient.

A pulse transit time (PTT) 618 is a measure of a temporal element of the pulse. For example, the PTT 618 may be a transit time of a given pulse from the heart to the location proximate where the PPG sensor 212 is positioned. The PTT 618 may be calculated by using an ECG system to detect the pulse at the heart and a PPG system to detect the pulse at the finger, and the time difference between the detection at the heart and the detection at the finger corresponds to the PPT 618. The PTT 618 may be calculated by using a dual-pleth system where two PPG sensors are attached at two different locations of the patient and measuring a differential time between detection of the pulse at the first PPG sensor and detection of the pulse at the second PPG sensor (e.g. at a finger and at an ear). The time difference between the pulse defections correspond to the PPT 618. Other methods of detecting and/or calculating the PPT 618 may be used in other embodiments. The PPT 618 may be affected by other physiological conditions of the patient, such as blood pressure, heart rate, respiration, and the like. The PTT 618 is variable depending on the physiological status of the patient.

A second pulse waveform 620 is illustrated in FIG. 6 and is represented by a dashed line along the waveform. Internal pulse components 622 of the second pulse are also illustrated by dashed lines of corresponding internal pulse components. A pulse period 624, defined by the heart rate (HR) of the patient, may be calculated by measuring the time difference between the pulses. For example, the pulse period 624 may be s measurement of the time difference from the initiation of the pulse waveform 600 to the initiation of the second pulse waveform 620. Alternatively, the pulse period 624 may be a measurement of the time difference from a peak 626 of the pulse waveform 600 to a peak 628 of the second pulse waveform 620. The pulse period 624 may be affected by other physiological conditions of the patient, such as blood pressure, heart rate, respiration, and the like. The pulse period 624 is variable depending on the physiological status of the patient.

In an embodiment, characteristics of the pulse waveform 600 may be useful in determining stroke volume, cardiac output or other physiological parameters of the patient. For example, the pulse trending module 249 may use a slope transit time 630 associated with the primary peak 602 to calculate stroke volume, cardiac output or other physiological parameters of the patient. The slope transit time 630 of the upslope of the primary peak 602 of the pulse waveform 600 corresponds to a gradient 632 of the upslope for a given amplitude 634 of the pulse waveform 600. As shown in FIG. 6, because the initial pressure wave 610 dominates the shape of the primary peak 602, particularly the upslope of the primary peak 602, the measured gradient 632, amplitude 634 and slope transit time 630 of the primary peak 602 can be assumed to be equivalent to a gradient (m), amplitude (A) and a slope transit time (STT) of the initial pressure wave 610.

The gradient m provides a measure of the upslope of the initial pressure wave 610. The gradient M is an amplitude change per unit time and may generally be represented by:

$$m = A/STT \qquad \text{Equation (1)}$$

where m is the gradient of the initial pressure wave 610, a is the amplitude of the initial pressure wave 610, and STT is the slope transit time of the initial pressure wave 610.

The inverse of the gradient m is the time change per unit amplitude and may generally be represented by:

$$k = 1/m \qquad \text{Equation (2)}$$

where k is the temporal gradient of the initial pressure wave 610. The temporal gradient k is proportional to STT and is not dominated by HR effects, as described in further detail below. Optionally, the temporal gradient k=STT. The temporal gradient k may be used by the pulse trending module 249 to calculate stroke volume. For example, SV may be a function of k (e.g., f(k)). The pulse trending module 249 may calculate SV according to the following equations:

$$SV = a(k) + b \qquad \text{Equation (3)}$$

$$SV = K(a(k) + b) \qquad \text{Equation (4)}$$

$$SV = a(\ln[k]) + b \qquad \text{Equation (5)}$$

where a and b are empirically-determined constants that may be determined through clinical examinations of patients, K is a calibration constant, and ln is the natural logarithm. The constants a, b and K may be dependent upon the nature of the subject and/or the nature of the signal detecting devices. The constants a, b and K may be computed from relationships derived from observed historical data (e.g., relationships with patient demographic data such as body mass index (BMI), height, weight, and the like) and/or measured signal characteristics (e.g., heart rate, PTT, differential PTT, and the like). The calibration constant K may be derived in whole or in part by calibration through dilution methods for obtaining stroke volume or cardiac output or other methods, after which the SV or CO may be calculated continuously using the calibrated equation of SV with respect to k.

In some embodiments, the PPG signal may be corrected or normalized to account for changes in vascular tone and/or motion artifacts through analysis of the PPG signal. Normalizing may be performed prior to calculating k.

Figure 7:
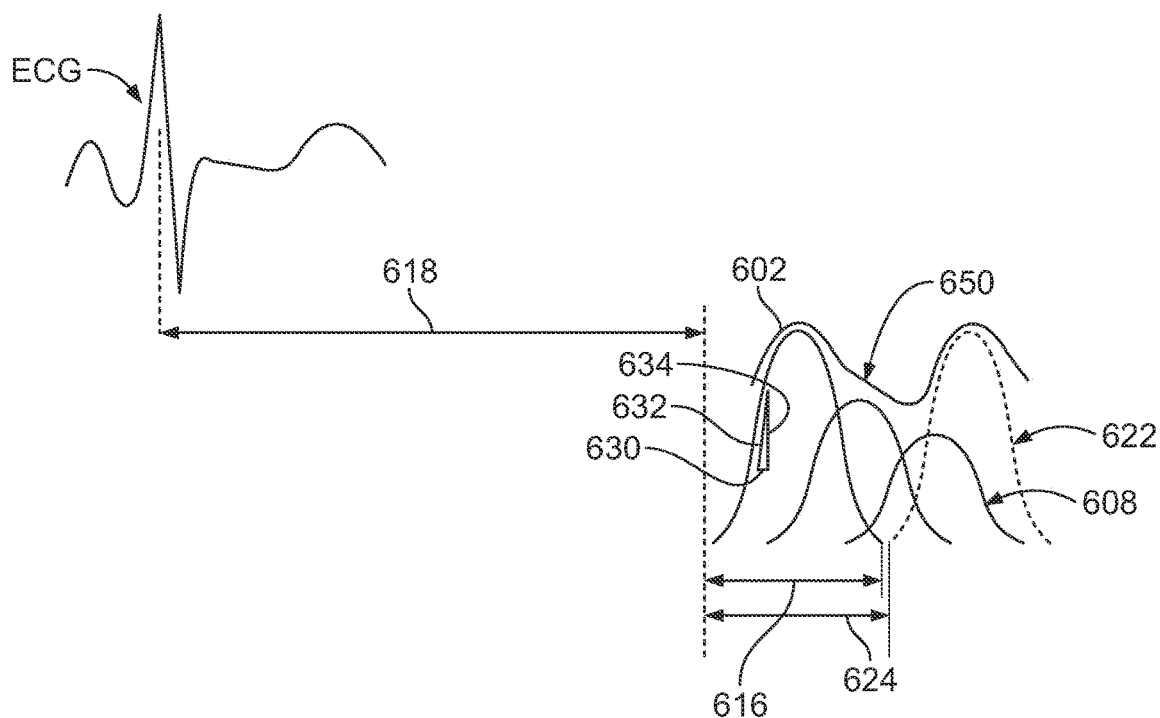
FIG. 7 illustrates a pulse waveform of a PPG signal according to an embodiment.

In some embodiments, the pulse trending module 249 may calculate the gradient m, amplitude A and/or slope transit time STT of the pressure wave 610 as a function of the measured gradient 632 and slope transit time 630, such as by predicting the effects of reflected waves of previous pulses based on wave periods, pulse periods, pulse transit limes, shapes of previous waveforms, and the like, FIG. 7 illustrates a pulse waveform 650 of a PPG signal, according to an embodiment. The pulse waveform 650 is similar to the pulse waveform 600 shown in FIG. 8, however the pulse waveform 650 is a pulse waveform taken during inhalation whereas the pulse waveform 600 is a pulse waveform taken during exhalation. In FIG. 7, like reference numerals from FIG. 6 are used to identify like components.

Comparison of the waveform characteristics between FIG. 6 and FIG. 7 illustrate how the pulse waveforms have two competing temporal elements that affect the pulse waveforms. For example, during exhalation (FIG. 8), the blood pressure is increasing but the heart rate is decreasing. During inhalation (FIG. 7), the opposite occurs where the blood pressure decreases and the heart rate increases. Owing exhalation (FIG. 6), as the blood pressure increases, the internal pulse waves travel faster, thus reducing PTT 618 and having shorter wave periods 616. However, the pulse period 624 lengthens as the heart rate decreases during the exhalation phase of the respiratory cycle. During inhalation (FIG. 7), as the blood pressure decreases, the internal pulse waves travel slower, thus increasing PTT 618 and having longer wave periods 616. However, the pulse period 624 shortens due to the increasing heart rate. The opposing temporal effects make analysis of the pulse waveforms difficult as the time measured between two separate fiducial points on a single pleth or pulse waveform may be pulled in competing directions.

As shown in FIGS. 6 and 7, the gradient 632 of the upslope of the primary peak 602 corresponds to the PTT 618 and wave period 616. As the PTT 618 and wave period 616 increase (e.g. during inhalation), the bend of the gradient is to decrease, whereas as the PTT 618 and wave period 618 decrease (e.g. during exhalation), the trend of the gradient is to increase. However, during both exhalation and inhalation, the gradients 632 of the upslopes associated with the primary peaks 602 closely follow the actual gradients m of the initial pressure waves 610. The measured gradients 632 are a close approximation of the actual gradients m of the pressure wave 610. Such correlation between the measured gradient 632 and the actual gradient m occurs because the initial pressure wave 610 dominates such temporal region of the resulting (aggregate) pleth cardiac pulse waveform. Measurements of the gradients 632 and STTs 630 over a fixed amplitude 634 (e.g. height change of the waveform) at a highly localized region along the upslopes of the primary peaks 602 eliminates the effect of the heart rate on the pulse waveforms 600, 660 that may influence a transit time calculated from two separated fiducial points on the waveform. The pulse trending module 249 (shown in FIG. 3) calculates the time period for the pulse waveform 600, 650 to increase a fixed amplitude, and uses such pulse trend to calculate SV, such as according to equation 3.

Figure 8:
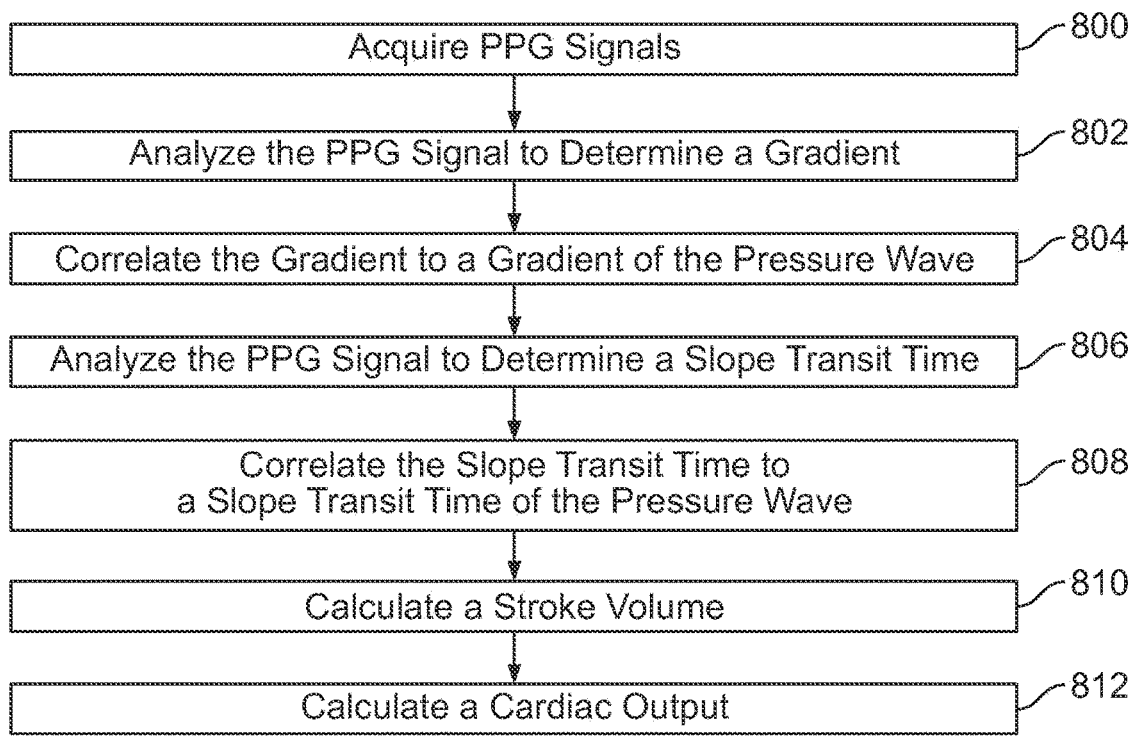
FIG. 8 illustrates a flow chart of a method of determining a stroke volume of a patient, according to an embodiment.

FIG. 8 illustrates a flow chart of a method of determining a stroke volume of a patient, according to an embodiment. The method may be performed by various systems, such as the system 100 (shown in FIG. 1), the system 210 (shown in FIGS. 2 and 3), or other capable systems. The method may include acquiring at 800 PPG signals. The PPG signals may be acquired by securing a PPG sensor to an anatomical portion of the pattern and sensing a physiological characteristic of the patient with the PPG sensor. While the embodiment of the method described herein references acquiring PPG senate, such as using the PPG sensor 212 (shown m FIG. 2), the method may include acquiring other types of physiological signals, such as ECG signals, PCG signals, and/or ultrasound signals that characterize or describe cardiac activity. The physiological signals may be obtained from the individual for at least a designated period of time.

In an embodiment, the PPG signal is analyzed by the pulse trending module 249 (shown in FIG. 3). The pulse trending module 249 analyzes the PPG signal to determine waveform characteristics of the PPG signal, such as an amplitude of the PPG signal, an amplitude trending component of the PPG signal (e.g., a change in amplitude per unit time, a rate of increase of the amplitude, a rate of decrease of the amplitude, and the like), a temporal component of the PPG signal, a temporal trending component of the PPG signal (e.g., a change in time per unit amplitude), and the like.

At 802, the PPG signal is analyzed to determine a gradient of the upslope of the primary peak of the PPG signal. The gradient may correspond to a fixed height change or amplitude of the PPG signal. Then, at 804, the system correlates the gradient of the primary peak to a gradient of the pressure wave. Because the PPG signal is an aggregation of pressure waves and reflected pressure waves, the system may determine or calculate the actual gradient of the pressure wave from the measured PPG signal. In an embodiment, because the initial pressure wave dominates the measured PPG signal at the upslope of the primary peak, the measured gradient may be assumed to be equal to the gradient of the pressure wave. In such embodiment, the system uses the measured gradient as the actual gradient. Alternatively, the system may calculate the actual gradient from the measured gradient by using a seating factor, an algorithm, a look-up table, or by other methods. Optionally, the system may calculate the gradient as a function of the measured gradient by predicting the effects of reflected waves of previous pulses based on wave periods, pulse periods, pulse transit times, shapes of previous waveforms, and the like.

Similarly, at 806, the PPG signal is analyzed to determine a slope transit time (STT) of the upslope of the primary peak of the PPG signal. The STT may correspond to a fixed height change or amplitude of the PPG signal. Then, at 806, the system correlates the STT of the primary peak to a STT of the pressure wave. Optionally, the system may determine the STT as an inverse of the gradient. For example, because the gradient m=A/STT, for a unit amplitude the STT=k=1/m.

At 810, a stroke volume is calculated based on the STT of the pressure wave. The stroke volume is calculated as a function of STT. The stroke volume may be calculated according to any of equations 3-6. The stroke volume may be calculated with a pleth-only system. For example, the system may be operated without the need for an invasive monitoring system, an ECG or any other monitoring system. The system may calculate the stroke volume with the use of a single PPG sensor. Further, the system, at 812, may calculate the cardiac output based on the stroke volume and the heart rate. For example, the CO=SV*HR.

Figure 9:
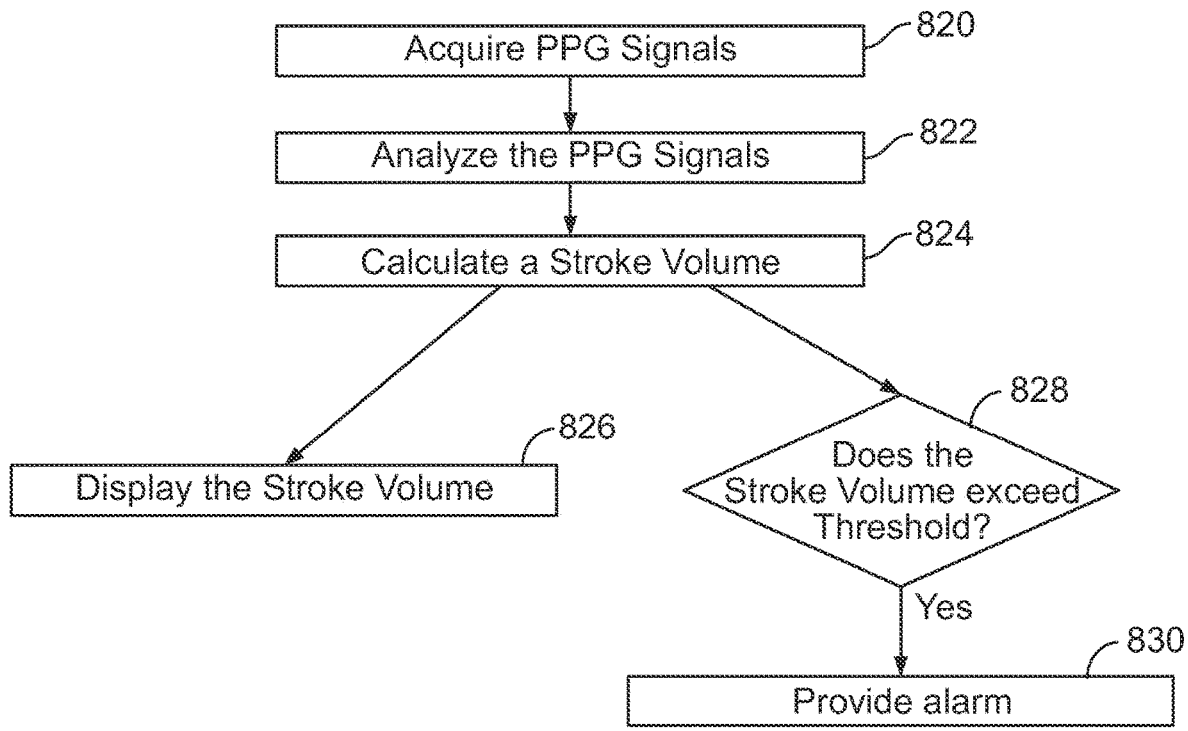
FIG. 9 illustrates a flow chart of a method of operating a PPG system, according to an embodiment.

FIG. 9 illustrates a flow chart of a method of operating a PPG system, according to an embodiment. The method may be performed by various systems, such as the system 100 (shown in FIG. 1), the system 210 (shown in FIGS. 2 and 3), or other capable systems. The method may include acquiring at 820 PPG signals. In an embodiment, the PPG signal is analyzed by the pulse trending module 249 (shown in FIG. 3). The pulse trending module 249 analyzes the PPG signal to determine waveform characteristics of the PPG signal.

At 822, the PPG signal is analyzed to determine an amplitude, a gradient and/or a slope transit time of the upslope of the primary peak of the pulse. Then, at 824, a stroke volume is calculated based on the STT of the pulse. The stroke volume is calculated as a function of STT. The stroke volume may be calculated according to any of equations 3-5.

At 826, the system displays the stroke volume on a monitor, such as the monitor 214 (shown in FIG. 2). The stroke volume may be displayed as a number, a grade, a graphical representation, and the like.

At 828, the system determines if the stroke volume exceeds a threshold. The threshold may be based on physiological conditions of the patient, such as age, weight, height, diagnosis, medications, treatments, and so forth. If the stroke volume exceeds the threshold, the system at 830 provides an alarm condition. The alarm may be a visual alarm, an audible alarm, or another type of alarm. The alarm may be triggered on the monitor 214 and/or may be transmitted to another location, such as a central monitoring station to alert medical professionals.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer of processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer," "computing system," or "module" may include any processor-based or microprocessor-based system including systems using microcontrollers, reduced instruction set computers (RISC), application specific integrated circuits (ASICs), logic circuits, and any other circuit or processor capable of executing the functions described hereto. The above examples are exemplary only, and are thus not intended to limit in any way the definition and/or meaning of the term "computer" or "computing system".

The computer, computing system, or processor executes a set of instructions that are stored to one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be to various forms such as system software or application software. Further, the software may be to the form of a collection of separate programs or modules, a program module within a larger program or a portion of a program module. The software also may include modular programming in the form of object-oriented programming. The processing of input data by the processing machine may be in response to user commands, or in response to results of previous processing, or to response to a request made by another processing machine.

As used hereto, the terms "software" and "firmware" are interchangeable, and include any computer program stored in memory for execution by a computer, including RAM memory, ROM memory, EPROM memory, EE PROM memory, and non-volatile RAM (NVRAM) memory. The above memory types are exemplary only, and are thus not limiting as to the types of memory usable for storage of a computer program.

As discussed above, embodiments may provide a system and method of determining a stroke volume of a patient through analysis of physiological signals, such as PPG signals, by analyzing waveform characteristics of the PPG signal and calculating a slope transit time of the PPG signal. The slope transit time is less influenced by momentary rises in the HR and is a good measurement tool for analyzing the PPG signal to determine stroke volume.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. While the dimensions, types of materials, and the like described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A photoplethysmogram (PPG) system comprising:
   a PPG sensor configured to generate a PPG signal including a primary peak separated from a trailing peak by a dicrotic notch, the PPG sensor comprising:
   one or more light sources configured to emit light into a tissue of a patient; and
   one or more detectors configured to detect an amount of the light from the tissue, wherein the detected amount of the light corresponds to a physiological characteristic of the patient,
   wherein the PPG sensor comprises a non-invasive PPG sensor; and
   processing circuitry configured to:
   receive the PPG signal from the PPG sensor, determine a slope transit time of an upslope of the primary peak of the PPG signal, and determine a stroke volume of the patient based on the determined slope transit time.

2. The PPG system of claim 1, wherein the processing circuitry is configured to determine the slope transit time of the upslope of the primary peak of the PPG signal by at least:

determining a contour of the PPG signal along the upslope of the primary peak, and determining the slope transit time based on an amplitude of the contour.

3. The PPG system of claim 1, wherein the processing circuitry is configured to determine the slope transit time by at least determining a gradient of the upslope for a given amplitude of the PPG signal.

4. The PPG system of claim 1, wherein the processing circuitry is configured to determine the slope transit time by at least determining a temporal gradient of the upslope, wherein the processing circuitry is configured to determine the slope transit time as a function of the temporal gradient.

5. The PPG system of claim 1, wherein the processing circuitry is configured to determine the stroke volume based on the determined slope transit time using one or more empirically determined constants.

6. The PPG system of claim 5, wherein the one or more empirically determined constants comprise a calibration constant.

7. The PPG system of claim 1, wherein the primary peak is indicative of a pressure wave, and wherein the processing circuitry is configured to determine the stroke volume based on the determined slope transit time by at least correlating the determined slope transit time to a slope transit time of another pressure wave.

8. The PPG system of claim 1, further comprising a display, wherein the processing circuitry is configured to present the stroke volume on the display.

9. The PPG system of claim 1, wherein the processing circuitry is further configured to:

determine the stroke volume is greater than a threshold, and trigger an alarm in response to determining the stroke volume is greater than the threshold.

10. The PPG system of claim 1, wherein the processing circuitry is configured to determine the stroke volume using sensed signals from only the non-invasive PPG sensor.

11. A method comprising:

receiving, by processing circuitry, a PPG signal from a PPG sensor, wherein the PPG sensor comprises a non-invasive PPG sensor;

determining, by the processing circuitry, a slope transit time of an upslope of a primary peak of the PPG signal;

determining, by the processing circuitry, a stroke volume of the patient based on the determined slope transit time;

presenting, by the processing circuitry, the stroke volume on a display;

determining, by the processing circuitry, that the determine stroke volume is greater than a threshold; and triggering, by the processing circuitry, an alarm in response to determining that the stroke volume is greater than the threshold.

12. The method of claim 11, wherein determining the slope transit time of the upslope of the primary peak of the PPG signal comprises:

determining a contour of the PPG signal along the upslope of the primary peak; and determining the slope transit time based on an amplitude of the contour.

13. The method of claim 11, wherein determining the slope transit time comprises determining a gradient of the upslope for a given amplitude of the PPG signal.

14. The method of claim 11, wherein determining the slope transit time comprises determining a temporal gradient of the upslope, and wherein determining the slope transit time comprises determining the slope transit time as a function of the temporal gradient.

15. The method of claim 11, wherein determining the stroke volume based on the determined slope transit time comprises determining the stroke volume based on the determined slope transit time and one or more empirically determined constants.

16. The method of claim 15, wherein the one or more empirically determined constants comprise a calibration constant.

17. The method of claim 11, wherein the primary peak is indicative of a pressure wave, and wherein determining the stroke volume based on the determined slope transit time comprises correlating the determined slope transit time to a slope transit time of another pressure wave.

18. The method of claim 11, wherein determining the stroke volume is based on sensed signals from only the non-invasive PPG sensor.

19. A photoplethysmogram (PPG) system comprising:

a non-invasive PPG sensor configured to generate a PPG signal including a primary peak separated from a trailing peak by a dicrotic notch, the PPG sensor comprising:

one or more light sources configured to emit light into a tissue of a patient; and one or more detectors configured to detect the light emitted from the one or more light sources, wherein the detected light corresponds to a physiological characteristic of the patient; and processing circuitry configured to:

receive the PPG signal from the PPG sensor, determine a contour of the PPG signal along an upslope of the primary peak, determine a slope transit time of the upslope of the primary peak of the PPG signal by at least:

determining a gradient of the upslope for a given amplitude of the PPG signal, or determining a temporal gradient of the upslope, and determine a stroke volume of the patient based on the determined slope transit time, wherein the processing circuitry is configured to determine the stroke volume based on sensed PPG signals from only the non-invasive PPG sensor.

20. The PPG system of claim 19, further comprising a display, wherein the processing circuitry is further configured to:

determine the stroke volume is greater than a threshold, and trigger an alarm on the display in response to determining the stroke volume is greater than the threshold.

* * * * *